United States Patent [19]

Juby et al.

[11] 4,031,093

[45] June 21, 1977

[54] 1,6-DIHYDRO-6-OXO-2-(ORTHO-SUBSTITUTED PHENYL)PYRIMIDINE-5-CARBOXYLIC ACID DERIVATIVES

[75] Inventors: Peter Frederick Juby, Jamesville; Richard Anthony Partyka, Liverpool, both of N.Y.

[73] Assignee: Bristol-Myers Company, New York, N.Y.

[22] Filed: Apr. 23, 1976

[21] Appl. No.: 679,630

Related U.S. Application Data

[63] Continuation-in-part of Ser. No. 611,765, Sept. 9, 1975, abandoned.

[52] U.S. Cl. .................. 260/251 R; 260/217.2 A; 260/247.2 B; 260/247.2 R; 260/251 A; 260/256.4 C; 424/251
[51] Int. Cl.$^2$ ........................................ C07D 239/22
[58] Field of Search ................ 260/251 R, 256.4 C

[56] References Cited

UNITED STATES PATENTS

| | | | |
|---|---|---|---|
| 3,660,403 | 5/1972 | Shen et al. | 260/251 R |
| 3,745,161 | 7/1973 | Shen et al. | 260/250 R |
| 3,883,653 | 5/1975 | Barth | 424/251 |

OTHER PUBLICATIONS

Ruhemann, "Ber.," vol. 30 (1897), pp. 821–823.
Cox et al., "Adv. in Drug Res.," vol. 5, 1970, pp. 115–196.
Mitter et al., "J. Indian Chem. Soc.," vol. 2 (1925), pp. 61–70.

*Primary Examiner*—Donald G. Daus
*Assistant Examiner*—James H. Turnipseed
*Attorney, Agent, or Firm*—David M. Morse

[57] ABSTRACT

A series of 1,6-dihydro-6-oxo-2-(ortho-substituted phenyl)pyrimidine-5-carboxylic acid derivatives is provided for use as inhibitors of allergic reactions. The compounds show antiallergy activity by both oral and parenteral routes of administration.

62 Claims, No Drawings

1,6-DIHYDRO-6-OXO-2-(ORTHO-SUBSTITUTED PHENYL)PYRIMIDINE-5-CARBOXYLIC ACID DERIVATIVES

CROSS-REFERENCE TO RELATED APPLICATION

This application is a continuation-in-part of co-pending application U.S. Ser. No. 611,765 filed Sept. 9, 1975, now abandoned.

BACKGROUND OF THE INVENTION

1. Field of the Invention:

This invention relates to certain 1,6-dihydro-6-oxo-2-(ortho-substituted-phenyl)pyrimidine-5-carboxylic acid derivatives and to their use as inhibitors of allergic reactions.

2. Description of the Prior Art:

Various medicinal agents have been employed in the treatment of allergic reactions such as bronchial asthma and allergic rhinitis which are believed to result mainly from antigenantibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the 1,6-dihydro-6-oxo-2(substituted-phenyl)pyrimidine-5-carboxylic acid derivatives of the present invention, the following references illustrate structurally related compounds known in the art.

1. Preparation of the unsubstituted acid and ester of the formula

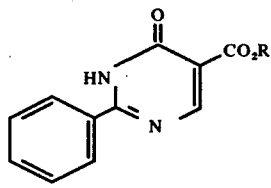

where R is hydrogen or ethyl is disclosed by S. Ruhemann in *Ber.*, 30, 821 (1897).

2. The p-methylphenyl and p-methoxyphenyl substituted esters and acids of the formula

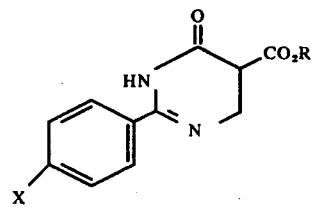

where R is hydrogen or ethyl and X is methyl or methoxy are disclosed by Mitter, et al. in *J. Chem. Soc.*, 123, 2179 (1923) and *Quart. J. Indian Chem. Soc.*, 2, 61 (1925).

3. Shen, et al., in U.S. Pat. Nos. 3,660,403 and 3,745,161 disclose compounds of the general formula

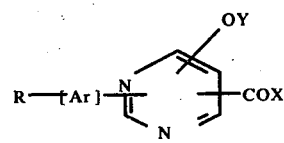

where R+Ar+ may inter alia be substituted phenyl, Y may be hydrogen and X is any of various substituents including hydroxy and alkoxy. The reference compounds are disclosed as having antiinflammatory, antipyretic and analgesic activity, and no mention is made of any utility as antiallergy agents. None of the compounds of the present invention is specifically disclosed in either of the Shen patents.

4. U.S. Patent 3,883,653 discloses antiallergy compounds of the formula

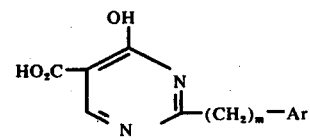

where m is an integer of 0 or 1 and Ar is pyridyl, thienyl, furyl, phenyl or phenyl substituted by hydroxy, methyl, methoxy, nitro, chloro, fluoro, 3,4-dimethoxy, 3,4,5-trimethoxy or alkanoylamino. None of the compounds of the present invention are disclosed in this reference.

SUMMARY OF THE INVENTION

This invention relates to new therapeutically useful 1,6-dihydro-6-oxo-2-(ortho-substitutedphenyl)pyrimidine-5-carboxylic acid derivatives, to processes for their preparation, to pharmaceutical compositions containing them and to methods for treating allergically-mediated diseases in mammals by administration of such derivatives or pharmaceutical compositions thereof. The compounds and compositions provided by the present invention are particularly valuable in the prophylactic treatment of allergic bronchial asthma by oral administration.

DETAILED DESCRIPTION OF THE INVENTION

The antiallergy agents of the present invention may be represented by the formula

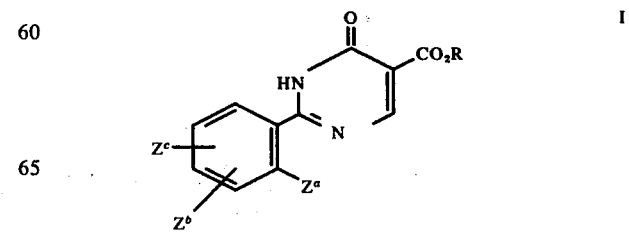

wherein $Z^a$ is $-O-C_1-C_6$ alkyl, $-O-C_2-C_6$ alkenyl, $$-O-(CH_2)_m-CH\underset{}{\overset{}{\diagup\diagdown}}(CH_2)_n$$

in which $m$ is 0 or an integer from 1 to 6 and $n$ is an integer from 2 to 7, $-OCH_2(CH_2)_xO(CH_2)_yCH_3$ in which $x$ and $y$ are each independently either 0 or an integer from 1 to 6, $-OCF_3$, $-OCH_2CF_3$, $-O(CH_2)_uCO_2R^a$ in which $u$ is an integer from 1 to 6 and $R^a$ is hydrogen or $C_1-C_6$ alkyl, $$R^b-\overset{O}{\underset{\|}{C}}-O-$$

in which $R^b$ is $C_1-C_6$ alkyl, $$-O-\overset{O}{\underset{\|}{C}}-NHR^b$$

in which $k$ is an integer from 2 to 6, $$-OCH_2-\underset{OH}{\overset{}{C}H}-CH_2OH \text{ or } -OCH_2-\underset{OH}{\overset{}{C}H}CH_2OCH_3,$$

$Z^b$ has the meaning stated above for $Z^a$ and in addition may be hydrogen, halogen, amino, $C_1-C_6$ alkylamino, di($C_1-C_6$)alkylamino, $$-N\underset{}{\overset{}{\diagup\diagdown}}(CH_2)_r$$

in which $r$ is 4 or 5, $$-N\underset{}{\overset{}{\diagup\diagdown}}O,$$

carb($C_1-C_6$)alkoxy, $C_1-C_6$ alkyl, $C_2-C_6$ alkenyl, $CF_3$, hydroxy, $C_1-C_6$ alkylthio, $R^c-CO-$ in which $R^c$ is $C_1-C_6$ alkyl or $R^c-CO-NH-$ in which $R^c$ is $C_1-C_6$ alkyl, $Z^c$ is hydrogen or $C_1-C_6$ alkoxy and R is hydrogen or the residue of an easily cleavable ester group, or a pharmaceutically acceptable salt thereof, provided that when $Z^a$ is methoxy, $Z^b$ and $Z^c$ are not hydrogen and when $Z^c$ is $C_1-C_6$ alkoxy, $Z^a$ and $Z^b$ are both $C_1-C_6$ alkoxy.

The $Z^b$ and $Z^c$ substituents on the compounds of formula I may be located at any of the other available positions of the phenyl ring, i.e. at the 3–6 positions. The substituents may be alike or different, but the only trisubstituted phenyl compounds (i.e. where $Z^c$ is not hydrogen) included within the scope of the invention are those where $Z^a=Z^b=Z^c=C_1-C_6$ alkoxy. The substituent groups disclosed above may be further defined as follows:

a. Halogen includes chlorine, bromine, fluorine and iodine. Preferred halogen substituents are chlorine and fluorine;

b. $C_1-C_6$ alkyl includes both straight and branched chain saturated aliphatic hydrocarbon radicals having from 1 to 6 carbon atoms inclusive, e.g. methyl, ethyl, n-propyl, isopropyl, n-butyl, isobutyl, sec-butyl and tert-butyl. Preferred substituents are those having from 1 to 4 carbon atoms;

c. $C_2-C_6$ alkenyl includes straight or branched chain unsaturated aliphatic hydrocarbon radicals containing one double bond and having from 2–6 carbon atoms inclusive, e.g. vinyl, allyl, isopropenyl, 2- or 3-methallyl or 3-butenyl;

d. $-O-C_1-C_6$ alkyl includes $C_1-C_6$ alkoxy radicals where the $C_1-C_6$ alkyl portion is as defined above under (a). Preferred alkoxy radicals are those having from one to four carbon atoms;

e. $-O-C_2-C_6$ alkenyl groups include radicals in which the $C_2-C_6$ alkenyl portion is as defined above in (c), e.g. vinyloxy, allyloxy or isopropenyloxy. A most preferred group is allyloxy;

f.

$$-O-(CH_2)_m-CH\underset{}{\overset{}{\diagup\diagdown}}(CH_2)_n$$

includes cycloalkyloxy and cycloalkyl-($C_1-C_6$)alkyloxy groups in which the cycloalkyl ring contains from 3 to 8 carbon atoms, preferably 3 to 6 carbon atoms. Examples of such groups are cyclopropyloxy, cyclobutyloxy, cyclopentyloxy, cyclohexyloxy, cycloheptyloxy, cyclopropylmethoxy, cyclobutylmethoxy, cyclobutylethoxy, cyclopentylmethoxy, cyclohexylmethoxy, cyclohexylethoxy, and cyclohexylpropoxy;

g. $-OCH_2(CH_2)_xO(CH_2)_yCH_3$ includes radicals such as $-OCH_2OCH_3$, $-OCH_2CH_2OCH_3$, $-OCH_2CH_2OCH_2CH_3$, $-OCH_2OCH_2CH_3$ and $-OCH_2CH_2CH_2OCH_2CH_3$;

h. $-O(CH_2)_uCO_2R^a$ represents radicals such as $-OCH_2CO_2H$, $-OCH_2CH_2CO_2H$, $-OCH_2CH_2CH_2CO_2H$, $-OCH_2CO_2CH_3$, $-OCH_2CO_2C_2H_5$, $-OCH_2CH_2CO_2CH_3$ and $-OCH_2CH_2CO_2C_2H_5$;

i.

$$R^c-\overset{O}{\underset{\|}{C}}-O-$$

includes $C_1-C_6$ acyloxy radicals such as $CH_3COO-$, $C_2H_5COO-$ and $C_3H_7COO-$;

j.

$$-O-\overset{O}{\underset{\|}{C}}-NHR^b$$

includes $C_1-C_6$ alkyl carbamoyloxy radicals such as $-OCONHCH_3$, $-OCONHC_2H_5$ and $-OCONHC_3H_7$;

k. $-O(CH_2)_kOH$ includes groups such as $-OCH_2CH_2OH$, $-O(CH_2)_3OH$ and $-O(CH_2)_4OH$;

l. $C_1-C_6$ alkylamino may be illustrated by such groups as methylamino, ethylamino, n-propylamino, etc.;

m. di($C_1-C_6$)alkylamino may be illustrated by dimethylamino, diethylamino, di-n-propylamino, etc.;

n.

$$-N\underset{}{\overset{}{\diagup\diagdown}}(CH_2)_r$$

includes pyrrolidino and piperidino;

o. carb($C_1-C_6$) alkoxy radicals include such groups as carbomethoxy, carbethoxy, carbopropoxy and carbobutoxy;

p. $C_1-C_6$ alkylthio includes alkylthio radicals such as methylthio, ethylthio, propylthio and butylthio;

q. $R^c-CO-$ is represented by such acyl groups as $C_2H_5CO-$, $C_3H_7CO-$ and $C_4H_9CO-$; and r. $R^c$—CO—NH— includes acylamino radicals such as $CH_3CONH$—, $C_2H_5CONH$— and $C_3H_7CONH$—.

A preferred embodiment of the present invention comprises the compounds of the formula

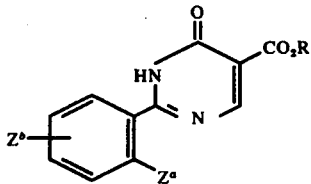
Ia wherein $Z^a$ is -O-$C_1$-$C_6$ alkyl,, -O-$C_2$-$C_6$ alkenyl, -O-$(CH_2)_m$-

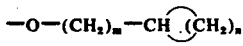

in which m is 0 or an integer from 1 to 6 and n is an integer from 2 to 7, —$OCH_2(CH_2)_xO(CH_2)_yCH_3$ in which x and y are each independently either O or an integer from 1 to 6, -$OCF_3$, —$OCH_2CF_3$, —$O(CH_2)_uCO_2R^a$ in which u is an integer from 1 to 6 and $R^a$ is hydrogen or $C_1$-$C_6$ alkyl, -$O(CH_2)_kOH$ in which k is an integer from 2 to 6,

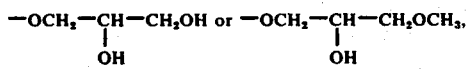

$Z^b$ has the meaning stated above for $Z^a$ and in addition may be hydrogen, halogen, amino, $C_1$-$C_6$ alkylamino, di($C_1$-$C_6$)alkylamino,

in which r is 4 or 5,

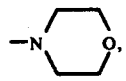

carb ($C_1$-$C_6$)alkoxy, $C_1$-$C_6$ alkyl, $C_2$—$C_6$ alkenyl, $CF_3$, hydroxy, $C_1$-$C_6$ alkylthio, $R^c$—CO— in which $R^c$ is $C_1$-$C_6$ alkyl or $R^c$—CO—NH— in which $R^c$ is $C_1$-$C_6$ alkyl, and R is hydrogen or the residue of an easily cleavable ester group, or a pharmaceutically acceptable salt thereof, provided that when $Z^a$ is methoxy, $Z^b$ is not hydrogen.

Within this group of compounds, a preferred subgroup comprises the compounds where $Z^b$ is fixed at the 5-position of the phenyl ring.

Another preferred embodiment comprises the compounds of the formula

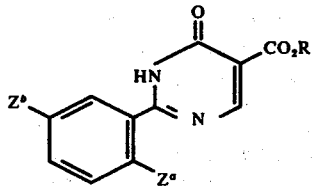
Ib wherein $Z^a$ is -O-$C_1C_6$ alkyl, -O-$C_2$-$C_6$ alkenyl or -O-$(CH_2)_m$—

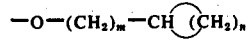

in which m is 0 or an integer from 1 to 4 and n is an integer from 2 to 5, $Z^b$ has the meaning stated above for $Z^a$ and in addition may be hydrogen, halogen, amino, $C_1$-$C_6$ alkylamino, di($C_1$-$C_6$)alkylamino,

in which r is 4 or 5,

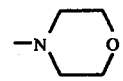

or carb($C_1$-$C_6$)alkoxy, or a pharmaceutically acceptable salt thereof. Within this group preferred subgroups are those in which a. $Z^a$ is —O—$C_1$—$C_6$ alkyl, most preferably ethoxy, n-propoxy, isopropoxy, n-butoxy, isobutoxy or sec-butoxy;

b. $Z^a$ is —O—$C_2$—$C_6$ alkenyl, most preferably allyoxy; and c. $Z^a$ is

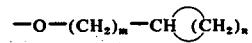

in which m is 0 or an integer from 1 to 4 and n is an integer from 2 to 5, most preferably cyclopropylmethoxy.

Another preferred embodiment comprises the disubstituted-phenyl esters of the formula

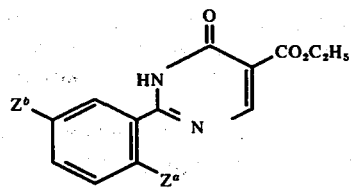
Ib' wherein $Z^a$ is methoxy, ethoxy, n-propoxy, isopropoxy, n-butoxy, isobutoxy, sec-butoxy, allyloxy or cyclopropylmethoxy and $Z^b$ is methoxy, ethoxy, n-propoxy, isopropoxy, n-butoxy, isobutoxy, sec-butoxy, allyloxy, cyclopropylmethoxy, chlorine, amino, dimethylamino or carbethoxy.

Another preferred embodiment comprises the disubstituted phenyl acids of the formula

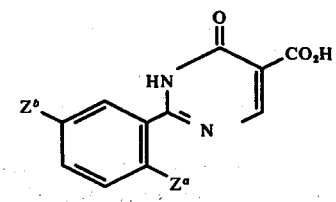
Ib'' wherein $Z^a$ is methoxy, ethoxy, n-propoxy, isopropoxy, n-butoxy, isobutoxy, sec-butoxy, allyloxy or cyclopropylmethoxy and $Z^b$ is methoxy, ethoxy, n-propoxy, isopropoxy, n-butoxy, isobutoxy, sec-butoxy, allyloxy, cyclopropylmethoxy, chlorine, amino, dimethylamino or carbethoxy, or a pharmaceutically acceptable salt thereof.

Another preferred embodiment comprises the monosubstituted phenyl compounds of the formula

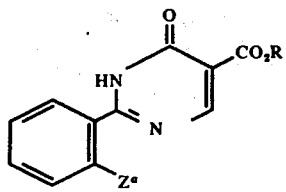

wherein $Z^a$ is —O—$C_2$—$C_6$ alkyl, -O-$C_2$-$C_6$ alkenyl,

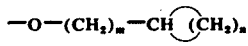

in which m is 0 or an integer from 1 to 6 and n is an integer from 2 to 7, —$OCH_2(CH_2)_xO(CH_2)_yCH_3$ in which x and y are each independently either 0 or an integer from 1 to 6, —$OCF_3$, —$OCH_2CF_3$, —$O(CH_2)_uCO_2R^a$ in which u is an integer from 1 to 6 and $R^a$ is hydrogen or $C_1$-$C_6$ alkyl, —$O(CH_2)_kOH$ in which k is an integer from 2 to 6,

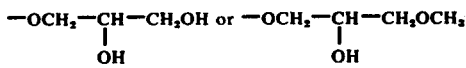

and R is hydrogen or the residue of an easily cleavable ester group or a pharmaceutically acceptable salt thereof.

Preferred sub-groups within the group of compounds defined by formula Ic include a. the compounds where $Z^a$ is —O—$C_2$—$C_6$ alkyl, —O—$C_2$—$C_6$ alkenyl or —O—$(CH_2)_m$—CH $(CH_2)_n$ in which m is 0 or an integer from 1 to 4 and n is an integer from 2 to 5, or a pharmaceutically acceptable salt thereof;

b. the compounds where $Z^a$ is ethoxy, n-propoxy, isopropoxy, n-butoxy, isobutoxy, sec-butoxy, allyloxy or cyclopropylmethoxy, or a pharmaceutically acceptable salt thereof.

c. the esters where R is $C_1$—$C_6$ alkyl;

d. the esters where R is pivaloyloxymethyl, acetoxymethyl or methoxymethyl;

e. the ethyl esters of the formula

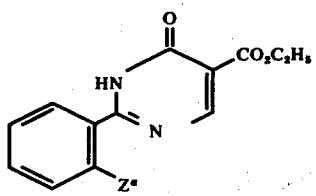

wherein $Z^a$ is ethoxy, n-propoxy, isopropoxy, n-butoxy, isobutoxy, sec-butoxy, allyloxy or cyclopropylmethoxy; and f. the 5-carboxylic acid compounds where $Z^a$ is ethoxy, n-propoxy, isopropoxy, n-butoxy, isobutoxy, sec-butoxy, allyloxy or cyclopropylmethoxy, or a pharmaceutically acceptable salt thereof.

Another preferred embodiment comprises the trisubstituted phenyl compounds of the formula

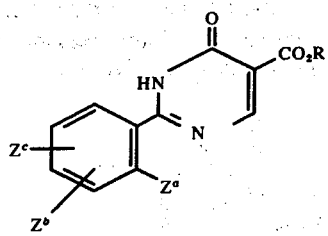

wherein $Z^a$, $Z^b$ and $Z^c$ are —O—$C_1$—$C_6$ alkoxy and R is hydrogen or the residue of an easily cleavable ester group, or a pharmaceutically acceptable salt thereof.

The compounds of formula I contain a basic functional group and, in some cases, a carboxyl functional group and are therefore capable of forming salts with both acids and bases. In employing the compounds as therapeutic agents, it is of course preferred to use pharmaceutically acceptable salts. Toxic salts may, however, be formed in the synthesis of the compounds and then converted to the desirable pharmaceutically acceptable salts by methods known per se. The pharmaceutically acceptable salts referred to above include salts within such bases as ammonia, organic amines and metal salts, e.g. metal salts containing sodium, potassium, calcium, magnesium, barium and aluminum cations. Representative of such bases are ammonia, primary amines such as n-propylamine, n-butylamine, ethanolamine, ethylenediamine, cyclohexylamine, benzylamine, ethylamine or octylamine, secondary amines such as diethanolamine, tertiary amines such as triethanolamine, N-methylpyrrolidine, N-methylmorpholine or 1,5-diazabicyclo-[4,3,0]-5-nonene and metal compounds such as sodium hydroxide, potassium hydroxide, ammonium hydroxide, sodium ethoxide, potassium methoxide, magnesium hydroxide, calcium hydroxide or aluminum hydroxide. Also included within the definition of pharmaceutically acceptable salts are the physiologically acceptable acid addition salts of the compounds of formula I, e.g. salts with mineral acids such as hydrochloric, hydrobromic phosphoric or sulfuric or organic acids such as maleic, acetic, citric, ascorbic, etc. Most preferred salts of the present invention are the sodium and potassium salts of the acids of formula I.

The compounds provided by the present invention may be prepared either in the form of a 5-carboxylic acid or as an easily cleavable ester, i.e. an ester group removable by methods such as chemical or enzymatic hydrolysis which do not result in any appreciable destruction of the remaining portion of the molecule. Examples of suitable esters are the $C_1$-$C_{10}$ alkyl esters (most preferably the $C_1$-$C_6$ alkyl esters) and physiologically cleaved esters such as pivaloyloxymethyl, acetoxymethyl and methoxymethyl which may find use as prodrugs in situations where a more prolonged administration of the antiallergy agent is desired.

Those skilled in the art will understand that the compounds represented by structural formula I are capable of also existing in the tautomeric forms shown below as formulae I' and I''. All of the forms I, I' and I'']may be present to a greater or lesser degree and are in a state of dynamic equilibrium with each other. While all of the various tautomeric forms are to be included within the scope of the present invention, the form represented by formula I has been arbitrarily used herein for the sake of convenience to describe the present compounds.

may even be eliminated as shown in the examples below.

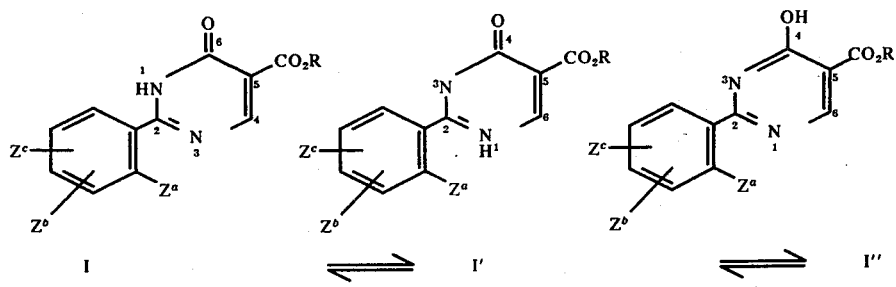

The compounds of formula I may be prepared by condensation of a substituted benzamidine of the formula

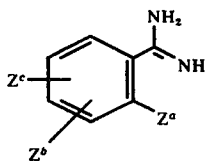

where $Z^a$, $Z^b$ and $Z^c$ are as defined above (in connection with compounds of formula I), or an acid addition salt thereof, with a compound of the formula

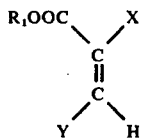

wherein $R_1$ is (lower)alkyl, i.e. $C_1$–$C_{10}$ alkyl, X is carb(lower)alkoxy or a group such as —C≡N convertible as by hydrolysis to carboxy and Y is a suitable leaving group such as —$OC_2H_5$, —$CH(COOC_2H_5)_2$,

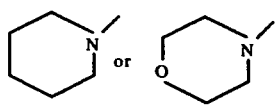

in an inert organic solvent and in the presence of a condensing agent and, optionally, cleaving the ester group at the 5-position of a so-produced compound and/or converting the so-produced compounds to easily cleavable esters or pharmaceutically acceptable salts thereof.

The condensation reaction is carried out in an inert organic solvent, e.g. a $C_1$–$C_6$ alcohol, acetonitrile or tetrahydrofuran and, advantageously, at elevated temperatures. Good results have been obtained when compounds II and III are refluxed in ethanol.

Starting materials II and III are generally reacted together in the presence of from at least a catalytic amount up to a several-fold molar excess of a suitable condensing agent. Alkali metal alkoxides (commonly prepared in situ by addition of the alkali metal to a $C_1$–$C_6$ alcohol) such as sodium methoxide are preferred condensing agents. When the benzamidine or benzamidine salt is condensed with diethyl ethoxymethylenemalonate, the alkali metal alkoxide condensing agent may be replaced by alkali metal carbonates or Benzamidine starting material II may be used either as the free base or as a salt thereof, e.g. the hydrochloride, fluorosulfonate or methyl sulfate salts. When the free base is employed, a molar equivalent or slight excess thereof of the alkali metal alkoxide is preferably used. If a benzamidine salt is used, two moles of alkoxide per mole of compound II are found to provide advantageous results. A preferred condensation procedure involves condensing the benzamidine or benzamidine salt (e.g. the methyl sulfate) with diethyl ethoxymethylenemalonate in an inert organic solvent (preferably ethanol) in the presence of about one mole of potassium carbonate per mole of benzamidine or salt thereof with heating, preferably at reflux temperature. Good results have also been obtained in the above procedure when the benzamidine free base is condensed with the diethyl ethoxymetylenemalonate in the absence of a condensing agent.

Compounds II and III are employed in approximately equimolar amounts. Schemes I–IV below illustrate condensation reaction procedures which are embodiments of the general process described above.

SCHEME I

A substituted benzamidine may be condensed with an alkyl dicarboxyglutaconate by the general method of S. Ruhemann in Ber. 30, 821 (1897). Illustrative of this procedure is the reaction

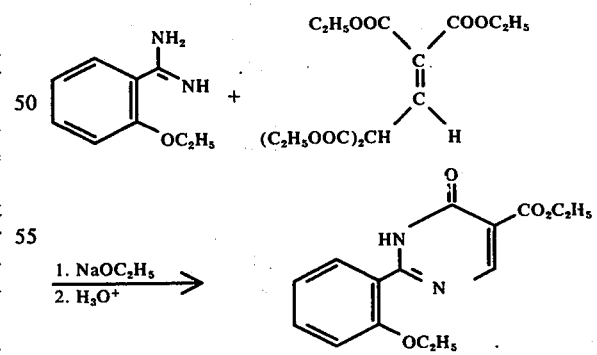

SCHEME II

The substituted benzamidine II is reacted with a dialkyl ethoxymethylenemalonate according to the general method described by P.C. Mitter, et al. in J. Chem. Soc., 123, 2179 (1923) and Quart. J. Indian Chem. Soc., 2, 61–70 (1925). Typifying this procedure is the sequence

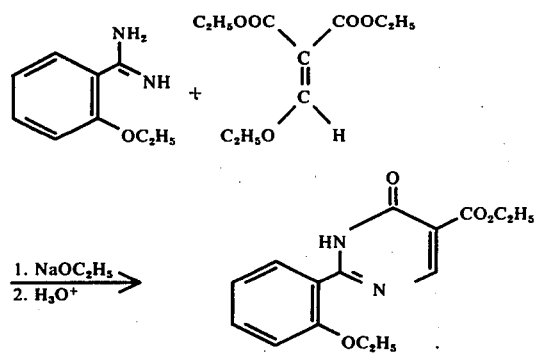

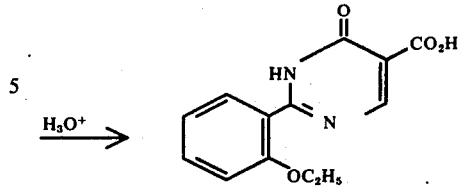

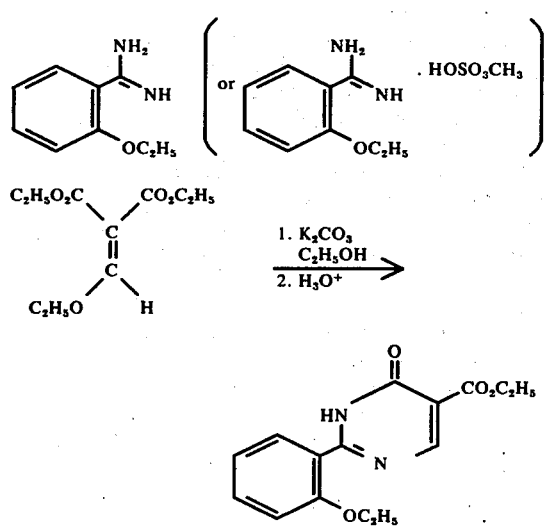

Reaction scheme II is illustrative of the preferred process for preparing the compounds of the present invention. As described above another preferred procedure involves the reaction

SCHEME III

A third variation of the general condensation reaction is to react the benzamidine II with an alkyl alkoxymethylenecyanoacetate according to the procedure described by P.C. Mitter, et al. in Quart. J. Indian Chem. Soc., 2, 61–70 (1925). The 5-cyanopyrimidine intermediate obtained may then be hydrolyzed with a mineral acid to give the desired 5-carboxylic acid. Illustrative of this procedure is the sequence

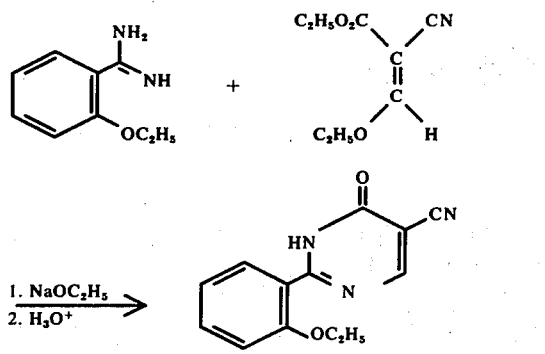

SCHEME IV

A fourth condensation procedure described by Santilli, et al. in J. Med. Chem., 7, 68 (1964) involves condensing the benzamidine with a dialkyl morpholinomethylenemalonate or a dialkyl piperidinomethylenemalonate. An example of this procedure is the reaction

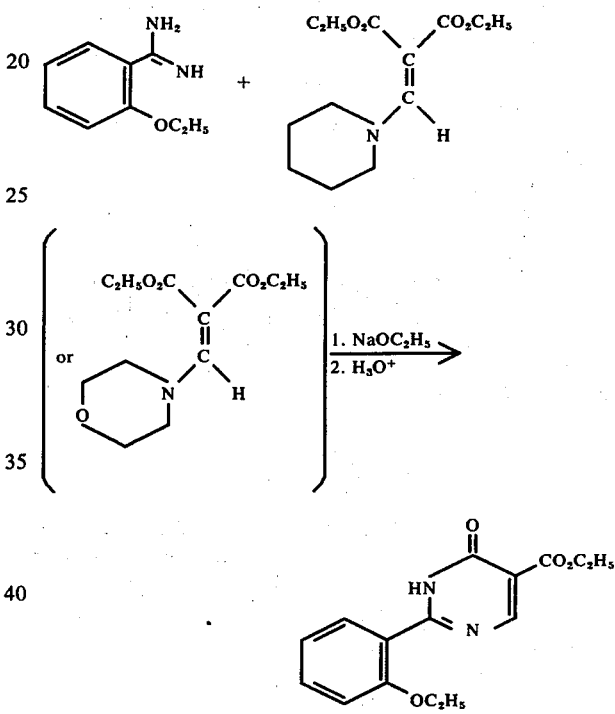

Use of an alkali metal condensing agent, e.g. $K_2CO_3$ or $NaOC_2H_5$, in the above procedures results in formation of a soluble alkali metal salt. Acidification of the reaction mixture with a mineral acid or an organic acid such as acetic acid will cause the desired ester of nitrile to precipitate out of solution.

At the conclusion of the condensation reaction the product obtained as a 5-carboxylic acid ester may be converted by methods known per se to the corresponding 5-carboxylic acid compound or to a pharmaceutically acceptable salt thereof. Thus, for example, the ethyl ester may be hydrolyzed under basic conditions to give a basic salt of the free acid compound which may then be neutralized with acid to obtain the free acid per se. A free acid compound of formula I may also be esterified by methods known per se to give a (lower)alkyl, i.e. $C_1-C_{10}$ alkyl ester or another easily cleavable ester such as pivaloyloxymethyl, acetoxymethyl or methoxymethyl.

The starting materials of formulae II and III are either known or are prepared by methods known in the art. One preferred procedure for synthesizing ortho substituted benzamidines is described in detail in the examples below and may be represented by the reaction sequence

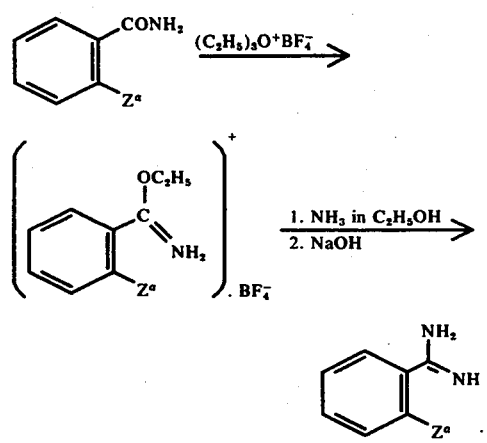

In this procedure which is described in U.S. Pat. No. 3,819,631 and *J. Org. Chem.*, 33, 1679 (1968), the triethyloxonium fluoroborate reactant mentioned above may be replaced by alkyl fluorosulfonates (e.g. methyl fluorosulfonate), dimethyl sulfate or by other alkyloxonium fluoroborates. A most preferred procedure involves use of the relatively inexpensive dimethyl sulfate $[(CH_3O)_2SO_2]$ as the alkylating agent in place of the more costly alkyl fluorosulfonates and triethyloxonium fluoroborate. This procedure which is outlined below results in formation of a benzamidine methyl sulfate salt.

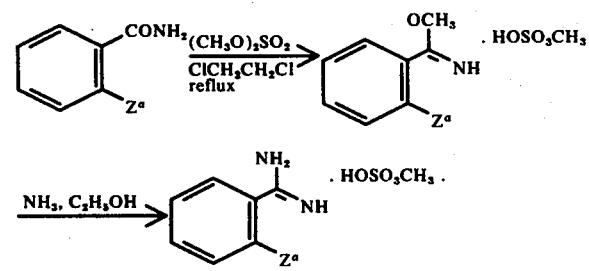

An alternative procedure for preparing ortho substituted starting materials of formula II is the reaction

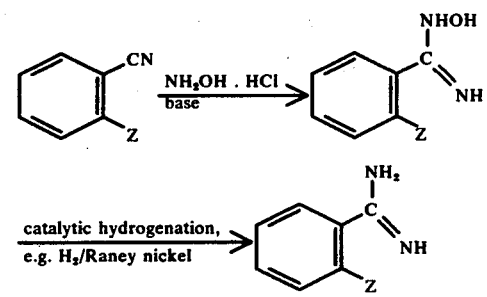

In preparing compounds of formula I in which $Z^a$, $Z^b$ or $Z^c$ contain free hydroxy, amino or carboxyl groups, it is of course understood that such groups are to be protected by suitable known protecting groups during the reaction steps beginning with the benzamide starting materials through the formation of the pyrimidine-5-carboxylate or carboxylic acid end-products. The protecting group(s) may then be removed by methods known per se to give the desired products having the unprotected substituent groups. In preparing compounds of formula I where $Z^b$ is $C_1$-$C_6$ alkylamino or di($C_1$-$C_6$) alkylamino, the corresponding amino-substituted compound may first be prepared and then alkylated by methods known per se. Alternatively, the dialkylamino-substituted compounds can be prepared directly from the appropriate benzamide starting material.

As noted previously, the compounds of formula I have been found to inhibit the release of toxic products, i.e. mediators, which arise from the combination of certain types of antibody and specific antigen. They are of particular value in preventing the symptoms of allergic bronchial asthma in mammalian subjects by administering to such subject a mediator-inhibiting dose of a compound of formula I. The compounds may also be useful for the relief and prophylaxis of other allergic reactons such as allergic rhinitis. reactions The compounds of the present invention may be administered either as individual therapeutic agents or as mixtures with other therapeutic agents. They may be administered alone but are generally administerd in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixers and aqueous solutions for injection. The compounds are most preferably administered in oral dosage forms.

The nature of the pharmaceutical composition and the pharmaceutical carrier of diluent will, of course, depend on the desired route of administration, i.e. orally, parenterally or by inhalation. Oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maizestarch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of formula I with conventional pharmaceutical vehicles may be employed, e.g. as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human asthmatic patients in single oral doses of approximately 1–500 mg. of active ingredient and multiple oral doses totalling up to about 1000 mg./day of active ingredient. When administered by inhalation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies described below indicate that the compounds of formula I are highly potent antiallergy agents. When administered orally in the rat PCA screening test, the compounds exhibit an unexpectedly superior activity relative to the antiallergy agents disclosed in U.S. Pat. 3,883,653.

Biological Activity Data

The reagin-mediated rat Passive Cutaneous Anaphylaxis (PCA) screening test used to evaluate the present compounds is generally regarded as one of the best animal models for use in predicting the antiallergy activity of test compounds in man. Briefly, the method consists of passive sensitization of skin sites on the test animals with reaginic antibodies followed after 24 hours by administration of the test drug and antigen challenge. The allergic response is measured by use of Evans' blue dye and is evaluated by the spot diameter at the injection site. Details of the test are provided below.

Materials

Ovalbumin (5 times crystalline)
Dinitrobenzene sulfonic acid, $Na^+$ salt
*Bordetella pertussis* vaccine - phase I $10-20 \times 10^9$ killed organisms/ml.
Aluminum hydroxide gel - 10 mg./ml.
Potassium carbonate
Male Sprague-Dawley (S/D) Rats - 200 gms.
Female Sprague-Dawley Rats - 100 gms.
Tris Buffered Saline (TBS) - 0.02 M 2-amino-2-hydroxymethyl-1,3-propanediol (Tris), 0.15 M NaCl, pH 8.2

Antigen Preparation - DNP-d EA

A substituted ovalbumin antigen is used both as immunogen and challenging antigen. The antigen is prepared as follows: 500 mg. ovalbumin (EA) and 500 mg. $K_2CO_3$ are dissolved in 25 ml. distilled $H_2O$ and stirred at room temperature for 5 minutes. Five hundred (500) mg. dinitrobenzene sulfonic acid, $Na^+$ salt, (previously recrystallized from hot absolute ethanol) is then added slowly with continued stirring. The reaction mixture is then immediately placed in the dark and allowed to proceed for 2 hours with constant stirring. After 2 hours the mixture is placed in suitable dialysis tubing and dialyzed against 5 changes (4 liters each) of distilled $H_2O$ at 5° C. After dialysis the product is lyophilized and stored at room temperature in a brown or amber container. The antigen obtained will appear as a light yellow, amorphous solid which is very soluble in water or saline. It is designated as DNP denatured ovalbumin (DNP-d EA).

Immunization Method for IgE Production

Adult, male Sprague-Dawley rats are used as a source of reagin-rich antisera for the PCA model. Immunization is by a combination of DNP-d EA on Al $(OH)_3$ gel and *B. pertussis* vaccine. Preparation of the DNP-d EA - gel immunogen is as follows: Dissolve the DNP-d EA in TBS so as to give a concentration of 10 mg./ml. Slowly add 1 ml. of this solution to 10 ml. Al(OH)$_3$ gel (10 mg. solids/ml.) with constant stirring at room temperature. Stir the mixture an additional 30 minutes to insure a uniform adsorption of antigen on gel.

The resulting preparation is then used in combination with phase I *B. pertussis* vaccine to immunize male S/D rats as follows: For each rat administer 0.1 ml. DNP-d EA - gel suspension intramuscularly in each hind leg (200 μg DNP-d EA and 2 mg. gel total dose). Follow these injections by the intraperitoneal administration of 1.0 ml. *B. pertussis* vaccine ($10-20 \times 10^9$ organisms). The use of light ether anesthesia during this procedure is recommended to insure proper intramuscular and intraperitoneal injections. Nine days following immunization (but no longer than 10) the animals are exsanguinated by cardiac puncture or abdominal aorta cannulation under ether or pentobarbital anesthesia. The collected whole blood is allowed to clot, the serum separated by centrifugation and the individual serum samples stored frozen until assayed for IgE content.

Selection of High Titered Serum Samples for Pooling

Individual serum samples should be screened for reaginic antibody concentration before being pooled with other sera, as not all rats respond to immunization procedures with reagin production. A 1:50 saline dilution of serum from each immunized rat is used for this purpose. Intradermal injections of 0.05 ml. of the diluted sera are made in the shaven backs of two small female recipient rats, 100-120 gms. Several serum samples can be tested simultaneously in recipient animals. After a 24 to 48 hour latent period antigen challenge is accomplished by intramuscular administration to each rat of 1 mg. DNP-d EA in 0.5 ml. 0.5% Evans' blue dye in saline. Sera which show positive PCA reactions at the 1:50 dilution, as measured 20 to 30 minutes post-challenge are pooled, dispensed in small aliquots and stored at −70° C. or lower until used. Negative sera may be discarded.

The IgE titer of the antisera pool should then be determined. Serial two-fold dilutions (1:5 to 1:160) of unheated sera and sera heated at 56° C. for 1 hour are prepared in saline and 0.05 ml of each dilution injected intradermally on the backs of female recipient rats. At least four animals should be used for both the heated and unheated serum titrations. After a 24-hour latent period each group is challenged with 1 mg. DNP-d EA in 0.5 ml. 0.5% Evans' blue dye. Reactions are read by reflecting the skin 20 to 30 minutes post-challenge. Intensity (blueing) and spot diameter should be measured and recorded. The pool titer is defined as the reciprocal of the greatest dilution of unheated serum which yields a measurable PCA response (>6 mm. diameter) in at least half of the recipient animals. Antiserum pools having a titer of 50 or greater are acceptable for the PCA screen. These pools should be sterile-filtered and stored at −70° C. or lower until use. Lyophilization in small aliquots may be used as an alternate.

PCA Screening Method

1. Animals - Young female Sprague-Dawley rats, 90-110 gms. should be used. The rats should be conditioned (acclimatized) for at least five days prior to use, with food and water ad lib.
2. Passive Sensitization - The test animals are prepared for passive sensitization by carefully shaving areas on each side of the back with a fine toothed clipper. Using a 27 gauge ⅝ inch needle mounted on a 1 ml. tuberculin syringe make intradermal injections of saline dilutions of the antiserum pool. Four dilutions (two on either side) of antiserum are used. The exact dilutions used depend on the titer of the pool. For example, if the antiserum pool has a titer of 50, then dilutions of 1:10, 1:20, 1:30 and 1:40 are used; if the pool titers at 100, then the dilutions would be 1:20, 1:40, 1:60 and 1:80. The sequence of placement of each dilution should be either clockwise or counter-clockwise to facilitate ease in scoring. The latent period should be at least 24 but no more than 48 hours.

3. Drug Administration-Standard and Unknowns - Four animals are used for each test compound. Disodium cromoglycate (DSCG), solubilized in saline, is administered by intravenous (i.v.) route at the time of antigen challenge. The ester test compounds are suspended in Tween/CMC. The carboxylic acid test compounds are solubilized in aqueous sodium bicarbonate. The test compounds are administered i.v. or per os (p.o.) either 1–5 or 10 minutes, respectively, prior to antigen challenge.

4. Antigen Challenge and Reaction Evaluation - Elicitation of the PCA response is accomplished by intravenous administration of 1 mg. DNP-d EA in 0.5 ml. 0.5% Evans' blue dye in saline to each test rat. PCA reactions are maximal twenty to thirty minutes post-challenge. Reactions should be scored visually for color intensity and the average diameter of the spots measured at each antiserum dilution site. Both operations should be done by reflecting the skin. For comparative purposes the numbers in the control group (untreated) should be at least 5%, and usually 10%, of the total animals tested on a particular day.

Observed drug inhibition is reported as percent reduction in effective antiserum titer in treated versus control groups.

Results

Test results for certain of the preferred compounds of the present invention by i.v. and p.o. routes of administration are shown below in Tables I and II along with data for DSCG. The results are given in terms of the $ID_{50}$ value, i.e. the dose of compound that inhibits 50% of the response.

Table I

Rat PCA Screening Data for Ethyl Esters

Compound

| Example No. | $Z^a$ | $Z^b$ | $ID_{50}$ in mg./kg. i.v. | p.o. |
|---|---|---|---|---|
| 1 | $OC_2H_5$ | H | 0.4 | ~2 |
| 5 | $OCH_2CH_2CH_3$ | H | — | ~5 |
| 7 | $OCH(_3)_2$ | H | — | ~2 |
| 9 | $O(CH_2)_3CH_3$ | H | — | 0.5 |
| 10 | $OCH(CH_3)CH_2CH_3$ | H | — | 0.5 |
| 12 | $OCH_2CH(CH_3)_2$ | H | — | ~3 |
| 8 | $OCH_2-CH=CH_2$ | H | — | 0.5 |
| 18 | $OCH_2-\triangleleft$ | H | — | ~0.3 |
| 15A | $OCH_3$ | $OCH_3$ | — | 5 |
| 15B | $OC_2H_5$ | Cl | — | ~0.5 |
| 16 | $OC_2H_5$ | $COOC_2H_5$ | — | 1 |
| 17 | $OC_2H_5$ | $NH_2$ | — | 0.5 |
| 15C | $OC_2H_5$ | $OCH_3$ | — | 0.3 |
| 19 | $OCH_2CH_2CH_3$ | $OCH_3$ | — | 0.7 |

Table I-continued

Rat PCA Screening Data for Ethyl Esters

Compound

| Example No. | $Z^a$ | $Z^b$ | $ID_{50}$ in mg./kg. i.v. | p.o. |
|---|---|---|---|---|
| DSCG | | | 0.3* | >>30 |

*Compound dosed at time of challenge

Table II

Rat PCA Screening Data for 5-Carboxylic Acids

Compound

| Example No. | $Z^a$ | $Z^b$ | $ID_{50}$ in mg./kg. i.v. | p.o. |
|---|---|---|---|---|
| 20 | $OC_2H_5$ | H | 0.07 | 0.5 |
| 21 | $OCH_2CH_2CH_3$ | H | ~0.1 | 0.9 |
| 22 | $OCH(CH_3)_2$ | H | — | 0.8 |
| 23 | $O(CH_2)_3CH_3$ | H | — | 0.5 |
| 24B | $OCH(CH_3)CH_2CH_3$ | H | — | 0.5 |
| 24C | $OCH_2CH(CH_3)_2$ | H | — | 0.5 |
| 24A | $OCH_2-CH=CH_2$ | H | — | 0.5 |
| 25 | $OCH_2-\triangleleft$ | H | — | ~0.1 |
| 24D | $OCH_3$ | $OCH_3$ | — | 1 |
| 24E | $OC_2H_5$ | Cl | — | 0.5 |
| 24F | $OC_2H_5$ | $NH_2$ | — | 0.9 |
| 24G | $OC_2H_5$ | $OCH_3$ | — | 0.2 |
| 27 | $OCH_2CH_2CH_3$ | $OCH_3$ | — | 0.3 |
| 26 | $OC_2H_5$ | $N(CH_3)_2$ | — | 0.3 |
| DSCG | | | 0.3* | >>30 |

*Compound dosed at time of challenge

The following examples are provided solely for the purpose of illustrating preparation of the starting materials and compounds of the present invention and are not to be construed as limitations of the invention. All temperatures referred to below are in degrees Centigrade. "Skellysolve B" is a petroleum ether fraction of b.p. 60-68° C. consisting essentially of n-hexane (trade name of Skelly Oil Co.)

Preparation of Starting Materials

The substituted benzamidine (or benzamidine salt) starting materials may be prepared according to the procedures illustrated below.

Preparation 1

2-Ethoxybenzamidine hydrochloride

To a cooled (ice-water) solution of triethyloxonium fluoroborate (100 g., 0.53 mole) in 226 ml. of methylene chloride was added all at once a suspension of 2-ethoxybenzamide (87 g., 0.53 mole) in 915 ml. of methylene chloride. The resulting solution was stirred at room temperature for 36 hours. The solution was concentrated to one-third volume and diluted with about 600 ml. of diethyl ether, thereby precipitating the crude ethyl 2-ethoxybenzimidate fluoroborate (130 g., m.p. 116°–133°).

The above salt was suspended in 500 ml. of cold 10% ethanolic ammonia and the solution stirred at room temperature for 36 hours. The solution was reduced to dryness and the residue partitioned between ethyl acetate and 5N NaOH. The ethyl acetate layer was dried to give a viscous oil. About 200 ml. of acetonitrile was added to the oil whereupon a solid separated and was recovered to yield 36 g. of material, melting at 180–183°. The solid was dissolved in about 60 ml. of methanol and acidified with hydrogen chloride. Addition of about 1 liter of dry ether precipitated the desired hydrochloride salt (31.2 g., m.p. 198°–199°).

PREPARATION 2

2-Ethoxybenzamidine hydrochloride (alternate procedure)

Methyl fluorosulfonate (14.5 g., 0.127 mole) was added to a solution of 2-ethoxybenzamide (20.0 g., 0.121 mole) in methylene chloride (324 ml.). After 3 hours the solvent was removed under reduced pressure. The residue was triturated with diethyl ether and the mixture filtered. The collected crude ethyl 2-ethoxybenzimidate fluorosulfonate (28.5 g.), m.p. 83°–110°, was added to saturated ammoniacal ethanol (120 ml.). The mixture was stirred at room temperature for four days. The mixture was filtered and the filtrate concentrated. The residue was triturated with 2N sodium hydroxide and the resulting mixture extracted with ethyl acetate. The extract was dried over sodium sulfate and then concentrated. A solution of the residual oil in acetonitrile (50 ml.) was treated with hydrogen chloride. Addition of diethyl ether (700 ml.) precipitated 2-ethoxybenzamidine hydrochloride (11.0 g., m.p. 193°–196°).

PREPARATION 3

2-Ethoxybenzamidine

To s solution of 2-ethoxybenzamide (13.0 g., 0.0785 mole) in 34 ml. of dry methylene chloride was added all at once a suspension of triethyloxonium fluoroborate (15.0 g., 0.0785 mole) in 137 ml. of methylene chloride. The solution which formed immediately upon addition of the fluoroborate was stirred for 19 hours at room temperature. The solution was concentrated to about one-third volume and diluted with about 100 ml. of diethyl ether to precipitate the ethyl 2-ethoxybenzimidate fluoroborate which, when collected and dried, weighed 19.2 g., m.p. 113°–116°.

The above imidate fluoroborate was then added to 100 ml. of ethanol containing 1.4 g. of $NH_3$. The resulting solution was stirred for 78 hours at room temperature while keeping the flask tightly stoppered. The solvent was removed under reduced pressure to give a colorless solid which was dissolved in a small volume of water and basified with 6N NaOH. After extraction with ethyl acetate, the solvent extract was dried to yield 7.4 g. of title product, m.p. 78°–84°.

Replacement of the 2-ethoxybenzamide used above by an equimolar amount of 2-isopropoxybenzamide or 2-n-propoxybenzamide gives 2-isopropoxybenzamidine and 2-n-propoxybenzamidine, respectively.

PREPARATION 4

2-Ethoxybenzamidine fluorosulfonate (Method A)

To a suspension of 2-ethoxybenzamide (500 g., 3.03 moles) in dry methylene chloride (8 l.) was added methyl fluorosulfonate (256 ml., 3.17 moles). The resulting solution was stirred at room temperature for 3 hours. The solvent was removed under vacuum. The residue was triturated with diethyl ether and the mixture filtered. The collected solid was washed with ether and then added to a cold (ice-water) solution of ammonia (500 g.) in ethanol (3 l.). The mixture was stirred in the cold for 0.5 hour and then at room temperature for 16 hours. The solution was concentrated and the residue crystallized from 1,2-dichloroethane to give 2-ethoxybenzamidine fluorosulfonate (517 g., 65%), m.p. 98°–99°.

Anal. Calcd. for $C_9H_{12}N_2O.HFSO_3$: C, 40.90; H, 4.96; N, 10.60. Found: C, 40.95; H, 4.83; N, 10.73.

PREPARATION 5

2-Ethoxybenzamidine fluorosulfonate (Method B)

To a suspension of 2-ethoxybenzamide (1 kg., 6.05 moles) in methylene chloride (12.5 l.) was added methyl fluorosulfonate (538 ml., 6.66 moles). The mixture was stirred at room temperature for 18.5 hours. Ammonia gas was then bubbled into this mixture for 8 hours while the temperature of the mixture was maintained below 26°. The mixture was stirred for an additional 16 hours at room temperature. The solvent was removed under vacuum to leave crude 2-ethoxybenzamidine fluorosulfonate (1.7 kg.).

PREPARATION 6

2-Ethoxybenzamidine methyl sulfate

A solution of 2-ethoxybenzamide (16.5 g., 0.1 mole) and dimethyl sulfate (19.0 ml., 0.2 mole) in 1,2-dichloroethane (60 ml.) was heated under reflux for 17 hours with stirring. The solvent was removed under reduced pressure. The residual oil was stirred for 0.5 hour with diethyl ether (200 ml.). The methyl 2-ethoxybenzimidate methyl sulfate was collected by filtration, dried, and then added to stirred, saturated ethanolic ammonia (150 ml.). The solution was allowed to stand at room temperature for 18 hours. The solution was filtered and the filtrate concentrated. The residue was triturated with diethyl ether after which the 2-ethoxybenzamidine methyl sulfate (19.9 g., 72% based on 2-ethoxybenzamide) was collected by filtration.

PREPARATION 7

2-n-Propoxybenzamidine hydrochloride

A.

Ethyl 2-n-Propoxybenzimidate fluoroborate

A solution of triethyloxonium fluoroborate (33.0 g., 0.175 mole) in methylene chloride (75 ml.) was added during 10 minutes to a stirred solution of 2-n-propoxybenzamide (31.3 g., 0.175 mole) in methylene chloride (150 ml.). The solution was stirred for an additional 18 hours at room temperature. The solution was concentrated to about one-fifth volume and was diluted with diethyl ether to precipitate the ethyl 2-n-propoxybenzimidate fluoroborate (44.0 g., 85% yield), m.p. 108°–112°.

B.

2-n-Propoxybenzamidine hydrochloride Ethanol (100 ml.) containing 6.5 g. of ammonia was added during five minutes to a stirred suspension of ethyl 2-n-propoxybenzimidate fluoroborate (44.0 g.) in ethanol (25 ml.). The resulting solution was stirred at 25° for 20 hours. The solution was reduced to dryness and the residue partitioned between diethyl ether and 5N sodium hydroxide. The ether layer was washed with brine, dried over sodium sulfate, and concentrated. A solution of the residue in ether (500 ml.) and ethanol (50 ml.) was treated with hydrogen chloride to precipitate 2-n-propoxybenzamidine hydrochloride (28.8 g., 76.6% yield), m.p. 184°–186.5°.

PREPARATION 8

2-n-Propoxybenzamidine methyl sulfate

The title compound (74% yield) was prepared from 2-n-propoxybenzamide in a manner similar to that described for the preparation of 2-ethoxybenzamidine methyl sulfate in Preparation 6 above.

Anal. Calcd. for $C_{11}H_{15}NO_2 \cdot CH_4O_4S$: N, 4.59. Found: N, 4.59.

PREPARATION 9

2-Isopropoxybenzamidine hydrochloride

A solution of triethyloxonium fluoroborate (38.4 g., 0.202 mole) in methylene chloride (75 ml.) was added during 15 minutes to a stirred solution of 2-isopropoxybenzamide (36.2 g., 0.202 mole) in methylene chloride (100 ml.). The mixture was stirred for 18 hours at room temperature. The solution was concentrated to about 1/15 volume and was diluted with diethyl ether to precipitate colorless crystals (60 g., m.p. 90°–110°) of crude ethyl 2-isopropoxybenzimidate fluoroborate. Recrystallization of this material from methylene chloride-diethyl ether gave 55 g. of colorless material, m.p. 114°–120°.

To a stirred suspension of the above fluoroborate (55 g.) in ethanol (50 ml.) was added 150 ml. of 8% ethanolic $NH_3$. The mixture was stirred for 64 hours at 25°. The solution was reduced to dryness and the residue made basic with 100 ml. of 5 N NaOH The basic mixture was extracted with ether and the ethereal extract dried. A solution of the residue in ether (500 ml.) and ethanol (50 ml.) was treated with hydrogen chloride to precipitate 24.1 g. of colorless 2-isopropoxybenzamidine hydrochloride, m.p. 162°–164°.

PREPARATION 10

2-n-Butoxybenzamidine hydrochloride

A solution of triethyloxonium fluoroborate (32.4 g., 0.171 mole) in methylene chloride (75 ml.) was added to a stirred solution of 2-n-butoxybenzamide [*J. Pharm. Pharmacol.*, 4, 872 (1952)] (33.0 g., 0.171 mole) in methylene chloride (200 ml.) at 25°. The mixture was stirred at 25° for 20 hours. The solution was concentrated to about 1/15 of the original volume and then diluted with diethyl ether. The precipitated solid was recrystallized from methylene chloride-diethyl ether to give ethyl 2-n-butoxybenzimidate fluoroborate (28.7 g.), m.p. 82°–88°. To a stirred, cooled (ice-water) suspension of the fluoroborate (28.7 g.) in ethanol (75 ml.) was added 8% ethanolic ammonia (150 ml.). The mixture was stirred at 25° for 20 hours. The ethanol was removed and the residue partitioned between ether and 5N sodium hydroxide (100 ml.). The ether layer was washed with brine, dried over sodium sulfate, and then concentrated. A solution of the residual oil in ether was treated with hydrogen chloride to precipitate the title compound (16.8 g.), m.p. 150°–155°.

PREPARATION 11

(±)-2-sec-Butoxybenzamidine hydrochloride

In a manner similar to that described for the preparation of 2-n-butoxybenzamidine hydrochloride in Preparation 10 above, (±)-2-sec-butoxybenzamidine hydrochloride, m.p. 142°–144°, was prepared from (±)-2-sec-butoxybenzamide which itself is disclosed in *J. Pharm. Pharmacol.*, 9, 855(1957).

PREPARATION 12

2-Isobutoxybenzamidine

A cold (ice-water) solution of 2-isobutoxybenzamide[1] (70.1 g., 0.363 mole) in methylene chloride (800 ml.) was added to a cold solution of triethyloxonium fluoroborate (69.0 g., 0.363 mole) in methylene chloride (175 ml.). The resulting solution was stirred at room temperature for 16 hours. Approximately two thirds of the solvent was removed and the residue diluted with diethyl ether (500 ml.). The mixture was filtered. The collected ethyl 2-isobutoxybenzimidate fluoroborate[1] (76.5 g.), m.p. 110°–112°, was added to ethanol (350 ml.) saturated with gaseous ammonia. After 67 hours at room temperature the solution was evaporated to dryness. The residue was treated with 5N sodium hydroxide (160 ml.). The mixture was extracted with methylene chloride (3 × 200 ml.) and the combined extracts were washed with water, dried (sodium sulfate) and concentrated. The residue was recrystallized from cyclohexane to give 2-isobutoxybenzamidine[1] (42.9 g., 61.5% overall), m.p. 49°–51°.

Anal. Calc'd for $C_{11}H_{16}N_2O$: C, 68.72; H, 8,39; N, 14.57. Found: C, 68.60; H, 8.42; N, 14.28. 6 Reference 1. B. J. Broughton, B. J. Large, S. M. Marshall, D. L. Pain and K. R. H. Wooldridge, U.S. Pat. No. 3,819,631 (1974).

PREPARATION 13

2-Isobutoxybenzamidine fluorosulfonate

Methyl fluorosulfonate (5.65 g., 0.0495 mole) was added to a stirred solution of 2-isobutoxybenzamide[1] (8.6 g., 0.0445 mole) in methylene chloride (100 ml.) under nitrogen. The solution was stirred at room temperature for 18 hours. Ammonia gas was then bubbled through the solution for 3 hours with stirring. The solution was concentrated and the residue recrystallized from 1,2-dichloroethane to give the title compound (1.1 g., 8.5% yield). Reference 1. B. J. Broughton, B. J. Large, S. M. Marshall, D. L. Pain and K. R. H. Wooldridge, U.S. Pat. No. 3,819,631 (1974).

PREPARATION 14

2-Ethoxy-5-methoxybenzamide hydrochloride

A. 2-Ethoxy-5-methoxybenzamide

5-Methoxysalicylamide (41.8 g., 0.250 mole) was dissolved in a solution of sodium (6.37 g., 0.277 g-atom) in ethanol (250 ml.). To the resulting cooled (ice-water) solution was added iodoethane (38.9 g., 0.250 mole) over a period of 20 minutes. The reaction mixture was allowed to warm to room temperature over 0.75 hour and then was heated under reflux for 19 hours. The mixture was concentrated and the residue triturated with water. The mixture was filtered and collected solid recrystallized from acetonitrile to give 2-ethoxy-5-methoxybenzamide (34.5 g., 70.7%), m.p. 128°–130°.

Anal. Calcd. for $C_{10}H_{13}NO_3$: C, 61.52; H, 6.71; N, 7.18. Found: C, 61.45; H, 6.51; N, 6.93.

B. 2-Ethoxy-5-methoxybenzamidine hydrochloride

Methyl fluorosulfonate (28.4 g., 0.248 mole) was added to a cooled (ice-water) solution of 2-ethoxy-5-methoxybenzamide (33.5 g., 0.172 mole) in methylene chloride (450 ml.) over a period of 20 minutes. The mixture was stirred at room temperature for 4 hours. Two thirds of the solvent was removed and the residue diluted with diethyl ether. The precipitated crude methyl 2-ethoxy-5-methoxybenzimidate fluorosulfonate (50.0 g.), m.p. 144°–152° was dissolved in cold ethanol (300 ml.) which had been saturated with ammonia. The mixture was stirred with cooling (ice-water) for 2 hours followed by 17 hours at room temperature. The ethanol was removed under reduced pressure to give a semi-solid which was treated with 5N sodium hydroxide (200 ml.). The mixture was extracted with ethyl acetate. The extract was dried (sodium sulfate) and concentrated. A solution of the residue in acetonitrile-acetone (2:5) was treated with hydrogen chloride gas to precipitate 2-ethoxy-5-methoxybenzamidine hydrochloride (10.5 g., 26.5%), m.p. 166°–167°.

PREPARATION 15

5-Carbomethoxy-2-ethoxybenzamidine

A: 5-Carbomethoxy-2-ethoxybenzamide

5-Carbomethoxy-2-ethoxybenzamide (m.p. 159°–161°) was prepared from 5-carbomethoxysalicylamide, iodoethane, and sodium methoxide in methanol in a manner analogous to that described for the preparation of 2-ethoxy-5-methoxybenzamide in Preparation 14A.

B: 5-Carbomethoxy-2-ethoxybenzamidine

5-Carbomethoxy-2-ethoxybenzamidine, m.p. 133°–135°, was prepared from 5-carbomethoxy-2-ethoxybenzamide in a manner similar to that described for the preparation of 2-isobutoxybenzamidine in Preparation 12.

PREPARATION 16

5-Chloro-2-ethoxybenzamidine hydrochloride

A: 5-Chloro-2-ethoxybenzamide

A mixture of 5-chlorosalicylamide (16.0 g., 0.093 mole), iodoethane (31.8 g., 0.204 mole), and potassium carbonate (13.1 g., 0.095 mole) in ethanol (225 ml.) was heated under reflux for 20 hours. The hot mixture was filtered. The filtrate was reduced to dryness. The residue was triturated with water. The mixture was filtered and the collected solid recrystallized from acetonitrile to give 5-chloro-2-ethoxybenzamide (6.8 g., 36.6%) m.p. 136°–139°.

Anal. Calcd. for $C_9H_{10}ClNO_2$: C, 54.15; H, 5.05; Cl, 17.76; N, 7.02. Found: C, 54.25; H, 4.85; Cl, 17.42; N, 6.89.

B: 5-Chloro-2-ethoxybenzamidine hydrochloride

If the procedure of Preparation 10 is repeated with the 2-n-butoxybenzamide used therein replaced by an equimolar amount of 5-chloro-2-ethoxybenzamide, there is produced the title product, m.p. 227° with decomposition.

Anal. Calcd. for $C_9H_{11}ClN_2O.HCl$: C, 45.97; H, 5.15; N, 11.91. Found: C, 46.23; H, 5.20; N, 11.87.

PREPARATION 17

2,5-Dimethoxybenzamidine hydrochloride

If the procedure of Preparation 10 is repeated with the 2-n-butoxybenzamide used therein replaced by an equimolar amount of 2,5-dimethoxybenzamide, there is produced the title product, m.p. 170°–172°.

PREPARATION 18

2-Cyclopropylmethoxybenzamidine hydrochloride

A: 2-Cyclopropylmethoxybenzamide

A stirred mixture of salicylamide (10.02 g., 0.074 mole), potassium carbonate (10.24 g., 0.074 mole) and bromomethylcyclopropane (10.0 g., 0.074 mole) in ethanol (15 ml.) was heated under reflux for 19 hours. The mixture was concentrated and the residue treated with water. The mixture was filtered and the collected solid recrystallized from benzene-Skellysolve B to give 2-cyclopropylmethoxybenzamide (10.0 g., 71.6%), m.p. 102°–105°.

B: 2-Cyclopropylmethoxybenzamidine hydrochloride

A solution of triethyloxonium fluoroborate (99.1 g., 0.522 mole) in methylene chloride (225 ml.) was added to a stirred solution of 2-cyclopropylmethoxybenzamide (99.2 g., 0.518 mole) in methylene chloride (450 ml.). The mixture was stirred at 22° for 18 hours. The solution was concentrated to about one-fifth volume and then diluted with diethyl ether. The precipitated solid was recrystallized from methylene chloride - diethyl ether to give ethyl 2-cyclopropylmethoxybenzimidate fluoroborate (104.7 g., 65.7%), m.p. 120°–121°. To a stirred, cooled (ice-water) mixture of the fluoroborate (104.7 g.) in ethanol (100 ml.) was added 400 ml. of 6% ethanolic ammonia. The mixture was stirred for 18 hours at 20°. The mixture was concentrated and the residue partitioned between diethyl ether and 3N sodium hydroxide. The ether layer was washed with brine and dried over sodium sulfate. The dried solution was treated with hydrogen chloride. The precipitate was recrystallized from methylene chloride-diethyl ether to give 2-cyclopropylmethoxybenzamidine hydrochloride (71.5 g., 92.5% from fluoroborate), m.p. 166°–171°.

PREPARATION 19

5-Methoxy-2-n-propoxybenzamidine hydrochloride

A: 5-Methoxy-2-n-propoxybenzamide

5-Methoxysalicylamide (56.0 g., 0.335 mole) was added to a cooled, stirred solution of sodium (8.55 g., 0.372 g-atom) in ethanol (335 ml.). To the resulting suspension was added 1-bromopropane (41.3 g., 0.335 mole) dropwise over 20 minutes. The mixture was stirred at room temperature for one hour, then was heated under reflux for 19 hours. The solvent was removed under reduced pressure. The residue was treated with cold water (500 ml.). The solid was collected by filtration and recrystallized from acetonitrile to give 5-methoxy-2-n-propoxybenzamide (29.0 g., 41.4%), m.p. 83°–87°.

Anal. Calcd. for $C_{11}H_{15}NO_3$: C, 63.14; H, 7.23; N, 6.69. Found: C, 63.28; H, 7.43; N, 6.47.

B: 5-Methoxy-2-n-propoxybenzamidine hydrochloride

To a solution of 5-methoxy-2-n-propoxybenzamide (29.0 g., 0.139 mole) in methylene chloride (200 ml.) at 5° was added methyl fluorosulfonate (15.8 g., 0.139 mole). The solution was stirred at room temperature for 5 hours. Most of the solvent was removed and the residual solution diluted with diethyl ether (500 ml.). The precipitated methyl 5-methoxy-2-n-propoxybenzimidate fluorosulfonate (35.4 g., m.p. 117°–126°) was collected and added to cold, saturated ethanolic ammonia (220 ml.). The mixture was stirred at room temperature for 19 hours. The solution was concentrated and the residual oil dissolved in a mixture of acetonitrile and ether. The resulting solution was treated with hydrogen chloride to precipitate 5-methoxy-2-n-propoxybenzamidine hydrochloride (31.5 g.) as an oil, which was separated by decantation of the solvents.

EXAMPLE 1

Ethyl 1,6-dihydro-6-oxo-2-(2-ethoxyphenyl)pyrimidine-5-carboxylate (illustrates use of benzamidine free base)

To a cooled solution of sodium (1.04 g., 0.045 g-atom) in 35 ml. of ethanol was added all at once 2-ethoxybenzamidine (7.4 g., 45 mmole). There was then added to this suspension over a 5 minute period a solution of diethyl ethoxymethylenemalonate (9.7 g., 45 mmole) in 20 ml. of ethanol whereupon a pale yellow precipitate soon formed. An additional 25 ml. of ethanol was added to the reaction mixture which was then heated under reflux for 2¼ hours. The cooled solution was poured into about 500 ml. of ice-water and acidified with 6N HCl to produce a pale yellow solid. The solid was dried to give 10.2 g., m.p. 144°–149°, of title product. Recrystallization from acetonitrile gave 9.8 g., m.p. 147°–150°, of purified product.

Anal. Calc'd for $C_{15}H_{16}N_2O_4$: C, 62.49; H, 5.60; N, 9.72. Found: C, 62.23; H, 5.57; N, 9.63.

EXAMPLE 2

Ethyl 1,6-dihydro-6-oxo-2-(2-ethoxyphenyl)pyrimidine-5-carboxylate (illustrates use of benzamidine hydrochloride salt)

To a cooled solution of sodium (8.2 g., 0.356 g-atom) in 300 ml. ethanol was added all at once 2-ethoxybenzamidine hydrochloride (35.7 g., 0.178 mole). A solution of diethyl ethoxymethylenemalonate (38.4 g., 0.178 mole) in 80 ml. of ethanol was added to the suspension and the mixture was heated under reflux for 2¼ hours. The cooled solution was added to about 2800 ml. of ice-water and the mixture was acidified to pH 5 with glacial acetic acid. The precipitated title product was dried to give 47 g. of an off-white solid, m.p. 147°–150°.

EXAMPLE 3

Ethyl 1,6-dihydro-6-oxo-2-(2-ethoxyphenyl)pyrimidine-5-carboxylate (illustrates use of benzamidine fluorosulfonate)

To a solution of sodium ethoxide at 18° prepared from sodium (41 g., 1.78 g-atoms) in ethanol (1 l.), was added a solution of 2-ethoxybenzamidine fluorosulfonate (206.5 g., 0.78 mole) in ethanol (500 ml.). The resulting solution was cooled to 13° and then treated with a solution of diethyl ethoxymethylenemalonate (180 ml., 0.89 mole) in ethanol (400 ml.). The mixture was heated under reflux for 2.25 hours. The mixture was cooled to 10° and then poured into cold water (5 l.) with good stirring. Ice was added as necessary to keep the temperature of the mixture below 20°. The mixture was acidified to pH 5 with glacial acetic acid. The solid material was collected by filtration, washed with water, and dried to give the title compound (218.7 g., 97%). Recrystallization from acetonitrile gave product with m.p. 144°–147°.

EXAMPLE 4

Ethyl 1,6-dihydro-6-oxo-2-(2-ethoxyphenyl)pyrimidine-5-carboxylate (illustrates most preferred procedure using benzamidine methyl sulfate)

2-Ethoxybenzamidine methyl sulfate (19.9 g., 0.072 mole) followed by diethyl ethoxymethylenemalonate (17.0 g., 0.079 mole) were added to a stirred solution of sodium (3.3 g., 0.144 g-atom) in ethanol (150 ml.). The mixture was heated under reflux for 2.25 hours. The cooled mixture was poured into ice-water (250 ml.) which was then acidified with glacial acetic acid. The title compound was collected by filtration, washed with water and dried. The product (16.0 g., 77%), had m.p. 138°–140°.

EXAMPLE 5

Ethyl 1,6-dihydro-6-oxo-2-(2-n-propoxyphenyl)pyrimidine-5-carboxylate (benzamidine hydrochloride)

2-n-Propoxybenzamidine hydrochloride (12.0 g., 0.0558 mole) was added to a stirred, cooled (ice-water) solution of sodium (2.57 g., 0.112 g-atom) in ethanol (50 ml.). To this cooled, stirred solution was added a solution of diethyl ethoxymethylenemalonate (12.1 g., 0.0558 mole) in ethanol (50 ml.) during 10 minutes. The mixture was heated under reflux for 2.5 hours. The cooled solution was poured onto ice and acidified with 6N hydrochloric acid. The precipitated ethyl 1,6-dihydro-6-oxo-2-(2-n-propoxyphenyl)pyrimidine-5-carboxylate (16.2 g., 96% yield) had m.p. 111°–113°. Two recrystallizations from cyclohexane gave title product with m.p. 112°–113°.

Anal. Calcd. for $C_{16}H_{18}N_2O_4$: C, 63.56; H, 6.00; N, 9.27. Found: C, 63.59; H, 6.15; N, 9.47.

EXAMPLE 6

Ethyl 1,6-dihydro-6-oxo-2-(2-n-propoxyphenyl)pyrimidine-5-carboxylate (benzamidine methyl sulfate with $K_2CO_3$)

A mixture of 2-n-propoxybenzamidine methyl sulfate 7.4 g., 0.0255 mole), potassium carbonate (3.53 g., 0.025 mole), and diethyl ethoxymethylenemalonate (5.99 g., 0.0277 mole) in ethanol (80 ml.) was heated under reflux with stirring for 17 hours. The cooled mixture was added to ice-water (160 ml.) which was then acidified with glacial acetic acid. The precipitate was collected by filtration, washed with water, and dried to give the title compound (6.55 g., 89%), m.p. 106°–107°.

EXAMPLE 7

Ethyl 1,6-dihydro-6-oxo-2-(2-isopropoxyphenyl)pyrimidine-5-carboxylate (benzamidine hydrochloride)

2-Isopropoxybenzamidine hydrochloride (10.0 g., 0.0465 mole) was added to a stirred, cooled (ice-water) solution of sodium 2.14 g., 0.093 g-atom) in ethanol (100 ml.). To this cooled, stirred solution was added dropwise a solution of diethyl ethoxymethylenemalonate (10.1 g., 0.0465 mole) in ethanol (30 ml.) over a 10 minute period. The mixture was refluxed for 2 hours and stored at 22° for 18 hours. The mixture was then poured onto ice-water containing acetic acid (10 ml.) and concentrated HCl (10 ml.) to precipitate the desired product. The precipitate was washed and dried to give 15.5 g. of the title product, m.p. 123°124°. Recrystallizations from ethyl acetate and then cyclohexane gave colorless crystals of the ester, m.p. 128°–130°.

Anal. Calcd. for $C_{16}H_{18}N_2O_4$: C, 63.56; H, 6.00; N, 9.27. Found: C, 63.60; H, 5.93; N, 9.29.

EXAMPLE 8

Ethyl 1,6-dihydro-6-oxo-2-(2-allyloxyphenyl)pyrimidine-5-carboxylate (benzamidine hydrochloride)

2-Allyloxybenzamidine hydrochloride[1] (19.07 g., 0.0896 mole) was added to a cooled (ice-water), stirred solution of sodium ethoxide (12.25 g., 0.18 mole) in ethanol (100 ml.). To this cooled, stirred mixture was added a solution of diethyl ethoxymethylenemalonate (19.4 g., 0.0896 mole) in ethanol (15 ml.). The mixture was heated under reflux for 2.5 hours and then allowed to stand at room temperature for 18 hours. The mixture was poured into ice-water containing acetic acid. The solid was collected and recrystallized from cyclohexane to give the title compound (24.0 g., 89%), m.p. 118°–120°. Recrystallization from cyclohexane gave product with m.p. 118.5°–120.5°.

Anal. Calcd. for $C_{16}H_{16}N_2O_4$: C, 63.99; H, 5.37; N, 9.33. Found: C, 63.93; H, 5.42; N, 9.36. 6 1. U.S. Pat. No. 3,819,631.

EXAMPLE 9

Ethyl 1,6-dihydro-6-oxo-2-(2-n-butoxyphenyl)pyrimidine-5-carboxylate (benzamidine hydrochloride)

The procedure of Example 8 was repeated except that the 2-allyloxybenzamidine hydrochloride used therein was replaced with an equimolar amount of 2-n-butoxybenzamidine hydrochloride. There was produced the title product, m.p. 123°–125°.

Anal. Calcd. for $C_{17}H_{20}N_2O_4$: C, 64.54; H, 6.37; N, 8.86. Found: C, 64.41; H, 6.29; N, 9.07.

EXAMPLE 10

Ethyl (±)-1,6-dihydro-6-oxo-2-(2-sec-butoxyphenyl)pyrimidine-5-carboxylate (benzamidine hydrochloride)

In a manner similar to that described for the preparation of ethyl 1,6-dihydro-6-oxo-2-(2-n-butoxyphenyl)pyrimidine-5-carboxylate in Example 9, ethyl (±)-1,6-dihydro-6-oxo-2-(2-sec-butoxyphenyl)pyrimidine-5-carboxylate, m.p. 134°–136°, was prepared from (±)-2-sec-butoxybenzamidine hydrochloride.

Anal. Calcd. for $C_{17}H_{20}N_2O_4$: C, 64.54; H, 6.37; N, 8.86. Found: C, 64.31; H, 6.12; N, 8.82.

EXAMPLE 11

Ethyl 1,6-dihydro-6-oxo-2-(2-isobutoxyphenyl)pyrimidine-5-carboxylate (benzamidine free base)

To a stirred sodium (3.15 g., 0.137 g-atom) in ethanol (250 ml.) was added 2-isobutoxybenzamidine (26.3 g., 0.137 mole) followed by diethyl ethoxymethylenemalonate (29.6 g., 0.137 mole). The mixture was heated under reflux for 3 hours. The cooled mixture was added to icewater (300 ml.) which was then acidified to pH 5 with glacial acetic acid. The crystalline product (36.4 g., 85%) m.p. 89°–91°, which formed on cooling was collected and a portion recrystallized from 50% aqueous ethanol to give the title compound, m.p. 92°–93°.

Anal. Calcd. for $C_{17}H_{20}N_2O_4$: C, 64.54; H, 6.37; N, 8.86. Found: C, 64.66; H, 6.64; N, 8.69.

EXAMPLE 12

Ethyl 1,6-dihydro-6-oxo-2-(2-isobutoxyphenyl)pyrimidine-5-carboxylate (benzamidine fluorosulfonate)

To a solution of sodium (161 mg., 7 mg-atoms) in ethanol (10 ml.) was added 2-isobutoxybenzamidine fluorosulfonate (1.02 g., 3.5 mmole). The mixture was warmed to give a clear solution to which was added a solution of diethyl ethoxymethylenemalonate (756 mg., 3.5 mmole) in ethanol (2 ml.). The solution was heated under reflux for 3 hours. The cooled mixture was added to ice-water (50 ml.) and was acidified to pH 5 with glacial acetic acid. After brief stirring, the solid was collected by filtration, washed with water, and dried to give the title compound (0.94 g., 86%), m.p. 90°–91°.

EXAMPLE 13

Ethyl 1,6-dihydro-6-oxo-2-(2-isobutoxyphenyl)pyrimidine-5-carboxylate (use of $K_2CO_3$ in place of alkali metal alkoxide)

Diethyl ethoxymethylenemalonate (6.42 g., 0.03 mole) was added to a stirred mixture of 2-isobutoxybenzamidine (5.76 g., 0.03 mole) and potassium carbonate (4.14 g., 0.03 mole) in ethanol (70 ml.). The mixture was heated under reflux for 4 hours. The cooled mixture was added to water (100 ml.) which was then acidified to pH 8 with 6N hydrochloric acid and then to pH 5 with glacial acetic acid. The title compound was collected by filtration, washed with water, and dried. The product (6.76 g., 71%) had m.p. 88°–90°.

EXAMPLE 14

Ethyl 1,6-dihydro-6-oxo-2-(2-isobutoxyphenyl)pyrimidine-5-carboxylate (coupling reaction without use of base condensing agent)

The experiment described above in Example 13 was repeated, but this time without the potassium carbonate. The title product was obtained in 69% yield, m.p. 89°–91°.

EXAMPLE 15

The following ethyl 1,6-dihydro-6-oxo-2-phenylpyrimidine-5-carboxylates were prepared from the corresponding benzamidine hydrochlorides according to the general procedures of Example 8.

A. Ethyl 1,6-dihydro-6-oxo-2-(2,5-dimethoxyphenyl)pyrimidine-5-carboxylate, m.p. 149°–150°.

Anal. Calcd. for $C_{15}H_{16}N_2O_5$: C, 59.20; H, 5.30; N, 9.21. Found: C, 59.07; H, 5.27; N, 9.23.

B. Ethyl 1,6-dihydro-6-oxo-2-(5-chloro-2-ethoxyphenyl)pyrimidine-5-carboxylate, m.p. 209°–212°.

Anal. Calcd. for $C_{15}H_{15}ClN_2O_4$: C, 55.82; H, 4,68; Cl, 10.99; N, 8.68. Found: C, 55.66; H, 4.76; Cl, 10.87; N, 8.78.

C. Ethyl 1,6-dihydro-6-oxo-2-(2-ethoxy-5-methoxyphenyl)pyrimidine-5-carboxylate, m.p. 149°–152°.

Anal. Calcd. for $C_{16}H_{18}N_2O_5$: C, 60.37; H, 5.70; N, 8.80. Found: C, 60.31; H, 5.68; N, 9.09.

EXAMPLE 16

Ethyl 1,6-dihydro-6-oxo-2-(5-carbethoxy-2-ethoxyphenyl)-pyrimidine-5-carboxylate (benzamidine free base)

Diethyl ethoxymethylenemalonate (1.18 g., 5.45 mmoles) was added to a cold, stirred mixture of sodium ethoxide (0.37 g., 5.45 mmoles) and 5-carbomethoxy-2-ethoxybenzamidine (1.21 g., 5.45 mmoles) in ethanol (15 ml.). The mixture was heated under reflux for 0.5 hours. The cooled mixture was poured onto ice-water and acidified with acetic acid. The precipitate was recrystallized from ethanol to give the title compound (1.49 g., 76%) as colorless crystals, m.p. 180°–181.5°.

Note that during the coupling reaction between the carbomethoxybenzamidine and the ethoxymethylenemalonate, ester exchange occurs (under the influence of the $NaOC_2H_5/C_2H_5OH$) resulting in the 5'-carbethoxy product.

EXAMPLE 17

Ethyl 1,6-dihydro-6-oxo-2-(5-amino-2-ethoxyphenyl)pyrimidine-5-carboxylate

A. Ethyl 1,6-dihydro-6-oxo-2-(2-ethoxy-5-nitrophenyl)pyrimidine-5-carboxylate Ethyl 1,6-dihydro-6-oxo-2-(2-ethoxyphenyl)pyrimidine-5-carboxylate (1.0 g., 3.46 mmoles) was added over a twenty minute period to a cooled (ice-water), stirred mixture of 70% nitric acid (1.7 ml., $d$=1.42) and 96% sulfuric acid (0.29 ml., $d$=1.84). The mixture was stirred at room temperature for 19 hours. The solution was poured into ice-water (300 ml.). The mixture was triturated and then filtered. The collected solid was recrystallized from acetonitrile to give the title compound (0.64 g., 55%), m.p. 222°–224°.

Anal. Calcd. for $C_{15}H_{15}N_3O_6$: C, 54.05; H, 4.54; N, 12.61. Found: C, 54.32; H, 4.71; N, 12.56.

B. Ethyl 1,6-dihydro-6-oxo-2-(5-amino-2-ethoxyphenyl)pyrimidine-5-carboxylate A mixture of ethyl 1,6-dihydro-6-oxo-2-(2-ethoxy-5-nitrophenyl)pyrimidine-5-carboxylate (0.42 g., 1.26 mmoles) and 10% palladium on carbon (0.07 g.) in ethanol (200 ml.) was treated with hydrogen at a pressure of about 3.5 kg./cm² until uptake of hydrogen ceased. The mixture was filtered and the filtrate reduced to dryness. The residue was recrystallized from water followed by aqueous ethanol to give the title compound (0.12 g., 31.6%), m.p. 107°–110°.

Anal. Calcd. for $C_{15}H_{17}N_3O_4 \cdot H_2O$: C, 56.07; H, 5.96; N, 13.08; $H_2O$, 5.62. Found: C, 56.37; H, 5.70; N, 13.32; $H_2O$, 5.82.

EXAMPLE 18

Ethyl 1,6-dihydro-6-oxo-2-(2-cyclopropylmethoxyphenyl)-pyrimidine-5-carboxylate The title compound was prepared from 2-cyclopropylmethoxybenzamidine hydrochloride in a manner similar to that described for the preparation of ethyl 1,6-dihydro-6-oxo-2-(2-allyloxyphenyl)pyrimidine-5-carboxylate in Example 8. The product had m.p. 104°–105°.

Anal. Calcd. for $C_{17}H_{18}N_2O_4$: C, 64.95; H, 5.77; N, 8.91. Found: C, 64.66; H, 5.93; N, 8.87.

EXAMPLE 19

Ethyl 1,6-dihydro-6-oxo-2-(5-methoxy-2-n-propoxyphenyl)-pyrimidine-5-carboxylate The title compound was prepared from 5-methoxy-2-n-propoxybenzamidine hydrochloride in a manner similar to that described for the preparation of ethyl 1,6-dihydro-6-oxo-2-(2-allyloxyphenyl)pyrimidine-5-carboxylate in Example 8. The product had m.p. 124°–126°.

Anal. Calcd. for $C_{17}H_{20}N_2O_5$: C, 61.43; H, 6.07; N, 8.43. Found: C, 61.39; H, 5.93; N, 8.34.

EXAMPLE 20

1,6-Dihydro-6-oxo-2-(2-ethoxyphenyl)pyrimidine-5-carboxylic acid

A solution of ethyl 1,6-dihydro-6-oxo-2-(2-ethoxyphenyl)pyrimidine-5-carboxylate (2 g., 6.9 mmole) in 1N NaOH (20 ml., 20 mmole) was heated at reflux for 10 minutes. The solution was cooled and acidified with 6N HCl to yield the title product (1.8 g., m.p. 168°–184°). Recrystallization from acetonitrile gave 1.2 g. of colorless crystals, m.p. 186°–188°.

Anal. Calcd. for $C_{13}H_{12}N_2O_4$: C, 59.99; H, 4.65; N, 10.76. Found: C, 59.85; H, 4.59; N, 10.67.

EXAMPLE 21

1,6-Dihydro-6-oxo-2-(2-n-propoxyphenyl)pyrimidine-5-carboxylic acid

A solution of ethyl 1,6-dihydro-6-oxo-2-(2-n-propoxyphenyl)pyrimidine-5-carboxylate (3.02 g., 0.01 mole) in 1N sodium hydroxide (22 ml.) was heated on a steam bath for 20 minutes. The cooled solution was treated with 1N hydrochloric acid (23 ml.). The precipitated 1,6-dihydro-6-oxo-2-(2-n-propoxyphenyl)-pyrimidine-5-carboxylic acid (2.67 g., 97.4% yield), m.p. 203°–206°, was recrystallized from ethanol to give product with m.p. 205.5°–207.5°.

Anal. Calcd. for $C_{14}H_{14}N_2O_4$: C, 61.31; H, 5.15; N, 10.21. Found: C, 61.33; H, 5.21; N, 10.38.

EXAMPLE 22

1,6-Dihydro-6-oxo-2-(2-isopropoxyphenyl)pyrimidine-5-carboxylic acid

A solution of ethyl 1,6-dihydro-6-oxo-2-(2-isopropoxyphenyl)pyrimidine-5-carboxylate (3.02 g.) in 1N NaOH (25 ml.) was heated on a steam bath for 15 minutes. The solution was acidified with 1N HCl (26 ml.) to precipitate 2.7 g. of the title acid, m.p. 191°–193°. Recrystallization from methanol gave pale yellow crystals of the acid, m.p. 193°–195°.

Anal. Calcd. for $C_{14}H_{14}N_2O_4$: C, 61.31; H, 5.15; N, 10.21. Found: C, 61.19; H, 5.02; N, 9.97.

EXAMPLE 23

1,6-Dihydro-6-oxo-2-(2-n-butoxyphenyl)pyrimidine-5-carboxylic acid

A mixture of ethyl 1,6-dihydro-6-oxo-2-(2-n-butoxyphenyl)pyrimidine-5-carboxylate (3.16 g., 0.01 mole), 1.0N sodium hydroxide (25 ml.), and 95% ethanol (10 ml.) was heated under reflux for 10 minutes. The hot solution was treated with charcoal and filtered. The filtrate was acidified with 1.0N hydrochloric acid (26 ml.) to precipitate the title compound (2.8 g., 97%), m.p. 163°–165°. Recrystallization from ethanol gave analytical product, m.p. 165°–166°.

Anal. Calcd. for $C_{15}H_{16}N_2O_4$: C, 62.49; H, 5.59; N, 9.72. Found: C, 62.36; H, 5.52; N, 9.89.

EXAMPLE 24

The following 1,6-dihydro-6-oxo-2-phenylpyrimidine-5-carboxylic acids were prepared from the corresponding ethyl-1,6-dihydro-6-oxo-2-phenylpyrimidine-5-carboxylates in a manner similar to that described for the preparation of 1,6-dihydro-6-oxo-2-(2-n-butoxyphenyl)pyrimidine-5-carboxylic acid in Example 23.

A. 1,6-Dihydro-6-oxo-2-(2-allyloxyphenyl)pyrimidine-5-carboxylic acid, m.p. 192°–194°.

Anal. Calcd. for $C_{14}H_{12}N_2O_4$: C, 61.76; H, 4.44; N, 10.29. Found: C, 61.87; H, 4.62; N, 10.22.

B. (±)-1,6-Dihydro-6-oxo-2-(2-sec-butoxyphenyl)pyrimidine-5-carboxylic acid, m.p. 142°–144°.

Anal. Calcd. for $C_{15}H_{16}N_2O_4$: C, 62.49; H, 5.60; N, 9.72. Found: C, 62.55; H, 5.63; N, 9.86.

C. 1,6-Dihydro-6-oxo-2-(2-isobutoxyphenyl)pyrimidine-5-carboxylic acid, m.p. 206°–207°.

Anal. Calcd. for $C_{15}H_{16}N_2O_4$: C, 62.49; H, 5.60; N, 9.72. Found: C, 62.31; H, 5.66; N, 9.50.

D.

1,6-Dihydro-6-oxo-2-(2,5-dimethoxyphenyl)pyrimidine-5-carboxylic acid, m.p. 268°–270°.

Anal. Calcd. for $C_{13}H_{12}N_2O_5$: C, 56.52; H, 4.38; N, 10.14. Found: C, 56.45; H, 4.30; N, 10.01.

E.

1,6-Dihydro-6-oxo-2-(5-chloro-2-ethoxyphenyl)pyrimidine-5-carboxylic acid, m.p. 234.5°–237°.

Anal. Calcd. for $C_{13}H_{11}ClN_2O_4$: C, 52.98; H, 3.76; Cl, 12.03; N, 9.51. Found: C, 52.86; H, 3.78; Cl, 11.90; N, 9.39.

F.

1,6-Dihydro-6-oxo-2-(5-amino-2-ethoxyphenyl)pyrimidine-5-carboxylic acid, m.p. 276° with decomposition.

Anal. Calcd. for $C_{13}H_{13}N_3O_4$: C, 56.72; H, 4.76; N, 15.27. Found: C, 56.66; H, 4.56; N, 15.09.

G.

1,6-Dihydro-6-oxo-2-(2-ethoxy-5-methoxyphenyl)pyrimidine-5-carboxylic acid, m.p. 176°–178°.

Anal. Calcd. for $C_{14}H_{14}N_2O_5$: C, 57.93; H, 4.86; N, 9.65. Found: C, 57.70; H, 4.66; N, 9.63.

EXAMPLE 25

1,6-Dihydro-6-oxo-2-(2-cyclopropylmethoxyphenyl)pyrimidine-5-carboxylic acid

The title compound was prepared from ethyl 1,6-dihydro-6-oxo-2-(2-cyclopropylmethoxyphenyl)pyrimidine-5-carboxylate in a manner similar to that described for the preparation of 1,6-dihydro-6-oxo-2-(2-n-butoxyphenyl)pyrimidine-5-carboxylic acid in Example 23. The product had m.p. 219°–220°.

Anal. Calcd. for $C_{15}H_{14}N_2O_4$: C, 62.93; H, 4.93; N, 9.79. Found: C, 62.92; H, 5.03; N, 9.73.

EXAMPLE 26

1,6-Dihydro-6-oxo-2-(5-dimethylamino-2-ethoxyphenyl)pyrimidine-5-carboxylic acid (alkylation of 5-amino product)

A solution (1.9 ml.) of 37% formaldehyde (23.8 mmoles) in water followed by sodium cyanoborohydride (450 mg., 7.15 mmoles) were added to a stirred solution of ethyl 1,6-dihydro-6-oxo-2-(5-amino-2-ethoxyphenyl)pyrimidine-5-carboxylate (720 mg., 2.38 mmoles) in acetonitrile (14 ml.). Glacial acetic acid (0.24 ml.) was then added over a period of one minute. The mixture was stirred at room temperature for 2 hours. Additional glacial acetic acid (0.24 ml.) was added and stirring was continued for an extra 0.5 hour. The mixture was treated with diethyl ether (35 ml.). The organic layer was washed with 10% aqueous sodium bicarbonate (3 × 10 ml.) followed by brine (30 ml.) and dried (sodium sulfate). The solvent was removed and a solution of the residue in acetonitrile-diethyl ether was extracted with 1 N sodium hydroxide (3 × 20 ml.). The aqueous extract was acidified with glacial acetic acid to pH 6. The precipitate was collected and recrystallized from acetonitrile to give the title compound (210 mg., 29%), m.p. 187°–196°. Recrystallization from benzene-Skellysolve B gave analytical material, m.p. 195°–198°.

Anal. Calcd. for $C_{15}H_{17}N_3O_4$: C, 59.39; H, 5.65; N, 13.86. Found: C, 59.23; H, 5.81; N, 13.91.

EXAMPLE 27

1,6-Dihydro-6-oxo-2-(5-methoxy-2-n-propoxyphenyl)pyrimidine-5-carboxylic acid

The title compound was prepared from ethyl 1,6-dihydro-6-oxo-2-(5-methoxy-2-n-propoxyphenyl)pyrimidine-5-carboxylate in a manner similar to that described for the preparation of 1,6-dihydro-6-oxo-2-(2-n-butoxyphenyl)pyrimidine-5-carboxylic acid in Example 23. The product had m.p. 185°–187°.

Anal. Calcd. for $C_{15}H_{16}N_2O_5$: C, 59.20; H, 5.30; N, 9.21. Found: C, 59.36; H, 5.35; N, 9.14.

EXAMPLE 28

Sodium 1,6-dihydro-6-oxo-2-(2-ethoxyphenyl)pyrimidine-5-carboxylate

To a stirred suspension of finely ground 1,6-dihydro-6-oxo-2-(2-ethoxyphenyl)pyrimidine-5-carboxylic acid (11.07 g., 0.0425 mole) in water (30 ml.) was added 2.05 N sodium hydroxide (20.8 ml., 0.0425 mole). The mixture was gently swirled while being heated to boiling. The hot solution was treated with charcoal and filtered. The filtrate was concentrated on a rotary evaporator until crystallization began. The mixture was then freeze dried. The solid was heated (bp of 95% ethanol) for four hours under vacuum (0.1 mm). The solid (m.p. 267°–270°) was allowed to equilibrate with the atmosphere for about 2 days.

Anal. Calc'd for $C_{13}H_{11}N_2NaO_4 \cdot H_2O$: C, 52.00; H, 4.36; N, 9.33. Found: C, 51.79; H, 3.75; N, 9.26.

Replacement of the 1,6-dihydro-6-oxo-2-(2-ethoxyphenyl)pyrimidine-5-carboxylic acid in the above procedure with equimolar amounts of 1,6-dihydro-6-oxo-2-(2-n-propoxyphenyl)pyrimidine-5-carboxylic acid and 1,6-dihydro-6-oxo-2-(2-isopropoxyphenyl)pyrimidine-5-carboxylic acid gives the sodium salts for each of the named acids.

Replacement of the sodium hydroxide in the above procedure with other bases, e.g. KOH, $Ca(OH)_2$, $Al(OH)_3$, $Ba(OH)_2$, $Mg(OH)_2$, gives the corresponding 5-carboxylic acid salts.

EXAMPLE 29

Potassium 1,6-dihydro-6-oxo-2-(2-ethoxyphenyl)pyrimidine-5-carboxylate

The potassium salt was prepared from 1,6-dihydro-6-oxo-2-(2-ethoxyphenyl)pyrimidine-5-carboxylic acid in a manner similar to that described for the preparation of the sodium salt in Example 28. After drying at 100° under vacuum the product had m.p. 247°–249° with decomposition.

Anal. Calc'd. for $C_{13}H_{11}KN_2O_4$: C, 52.34; H, 3.72; N, 9.39. Found: C, 52.62; H, 3.50; N, 9.18. (Corrected for 1.24% $H_2O$)

The procedures of Examples 28 and 29 can be used to make sodium and potassium salts of any of the 1,6-dihydro-6-oxo-2-phenylpyrimidine-5-carboxylic acids prepared according to the methods of the present invention.

EXAMPLE 30

1,6-Dihydro-6-oxo-2-(2-ethoxyphenyl)pyrimidine-5-carboxylic acid methyl ester To a mixture of 1,6-dihydro-6-oxo-2-(2-ethoxyphenyl)pyrimidine-5-carboxylic acid in methanol is added slowly and with stirring a catalytic amount of concentrated sulfuric acid. The mixture is heated under reflux for several hours and the excess methanol then removed. There is produced the title methyl ester.

When the 1,6-dihydro-6-oxo-2-(2-ethoxyphenyl)-pyrimidine-5-carboxylic acid of the above procedure is replaced by any of the other 5-carboxylic acid compounds of this invention, the corresponding methyl ester is produced.

When the methanol in the above procedure is replaced by other appropriate alcohols such as ethanol, propanol, isopropanol, butanol, isobutanol, etc., the corresponding ester is prepared.

We claim:

1. A compound of the formula

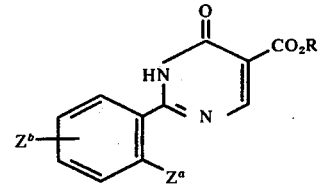

Ia wherein $Z^a$ is $-O-C_1-C_6$ alkyl, $-O-C_2-C_6$ alkenyl or

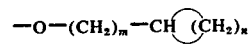

in which m is 0 or an integer from 1 to 6 and n is an integer from 2 to 7, $Z^b$ has the meaning stated above for $Z^a$ and in addition may be hydrogen, halogen, amino, $C_1-C_6$ alkylamino, di($C_1-C_6$)alkylamino, or carb($C_1-C_6$)alkoxy, and R is selected from the group consisting of hydrogen, $C_1-C_{10}$ alkyl, pivaloyloxymethyl, acetoxymethyl and methoxymethyl, or a pharmaceutically acceptable salt thereof, provided that when $Z^a$ is methoxy, $Z^b$ is not hydrogen.

2. A compound of the formula

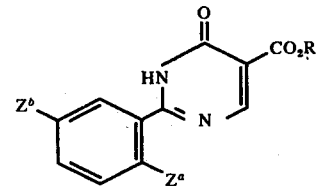

Ib wherein $Z^a$ is $-O-C_1-C_6$ alkyl, $-O-C_2-C_6$ alkenyl, or

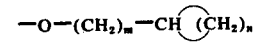

in which m is 0 or an integer from 1 to 6 and n is an integer from 2 to 7, $Z^b$ has the meaning stated above for $Z^a$ and in addition may be hydrogen, halogen, amino, $C_1-C_6$ alkylamino, di($C_1-C_6$)alkylamino, and R is selected from the group consisting of hydrogen, $C_1-C_{10}$ alkyl, pivaloyloxymethyl, acetoxymethyl and methoxymethyl, or a pharmaceutically acceptable salt thereof, provided that when $Z^a$ is methoxy, $Z^b$ is not hydrogen.

3. A compound of claim 2 wherein $Z^a$ is $-O-C_1-C_6$ alkyl, $-O-C_2-C_6$ alkenyl or

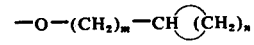

in which m is 0 or an integer from 1 to 4 and n is an integer from 2 to 5, $Z^b$ has the meaning stated above for $Z^a$ and in addition may be hydrogen, halogen, amino, $C_1-C_6$ alkylamino, di($C_1-C_6$)alkylamino, or carb(-$C_1-C_6$)alkoxy, or a pharmaceutically acceptable salt thereof.

4. A compound of claim 2 wherein $Z^a$ is $-O-C_1-C_6$ alkyl and $Z^b$ is $-O-C_1-C_6$ alkyl, $-O-C_2-C_6$ alkenyl,

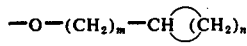

in which m is 0 or an integer from 1 to 4 and n is an integer from 2 to 5, hydrogen, halogen, amino, $C_1$–$C_6$ alkylamino, di($C_1$–$C_6$)alkylamino, or carb($C_1$–$C_6$)alkoxy, or a pharmaceutically acceptable salt thereof.

5. A compound of claim 4 wherein $Z^a$ is ethoxy, or a pharmaceutically acceptable salt thereof.

6. A compound of claim 4 wherein $Z^a$ is n-propoxy, or a pharmaceutically acceptable salt thereof.

7. A compound of claim 4 wherein $Z^a$ is isopropoxy, or a pharmaceutically acceptable salt thereof.

8. A compound of claim 4 wherein $Z^a$ is n-butoxy, or a pharmaceutically acceptable salt thereof.

9. A compound of claim 4 wherein $Z^a$ is isobutoxy, or a pharmaceutically acceptable salt thereof.

10. A compound of claim 4 wherein $Z^a$ is sec-butoxy, or a pharmaceutically acceptable salt thereof.

11. A compound of claim 2 wherein $Z^a$ is —O—$C_2$—$C_6$ alkenyl and $Z^b$ is —O—$C_1$—$C_6$ alkyl, —O—$C_2$—$C_6$ alkenyl,

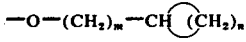

in which m is 0 or an integer from 1 to 4 and n is an integer from 2 to 5, hydrogen, halogen, amino, $C_1$–$C_6$ alkylamino, di($C_1$–$C_6$)alkylamino, or carb($C_1$–$C_6$)alkoxy, or a pharmaceutically acceptable salt thereof.

12. A compound of claim 11 wherein $Z^a$ is allyloxy, or a pharmaceutically acceptable salt thereof.

13. A compound of claim 2 wherein $Z^a$ is

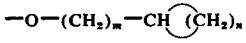

in which m is 0 or an integer from 1 to 4 and n is an integer from 2 to 5 and $Z^b$ is —O—$C_1$—$C_6$ alkyl, —O—$C_2$—$C_6$ alkenyl,

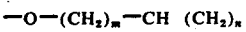

in which m is 0 or an integer from 1 to 4 and n is an integer from 2 to 5, hydrogen, halogen, amino, $C_1$–$C_6$ alkylamino, di($C_1$–$C_6$) alkylamino, alkoxy, or a pharmaceutically acceptable salt thereof.

14. A compound of claim 13 wherein $Z^a$ is cyclopropylmethoxy, or a pharmaceutically acceptable salt thereof.

15. A compound of the formula

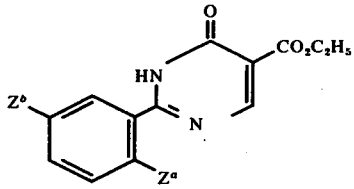

Ib' wherein $Z^a$ is methoxy, ethoxy, n-propoxy, isopropoxy, n-butoxy, isobutoxy, sec-butoxy, allyloxy or cyclopropylmethoxy and $Z^b$ is methoxy, ethoxy, n-propoxy, isopropoxy, n-butoxy, isobutoxy, sec-butoxy, allyloxy, cyclopropylmethoxy, chlorine, amino, dimethylamino or carbethoxy.

16. A compound of claim 15 wherein $Z^a$ is ethoxy and $Z^b$ is chlorine.

17. A compound of claim 15 wherein $Z^a$ is ethoxy and $Z^b$ is carbethoxy.

18. A compound of claim 15 wherein $Z^a$ is ethoxy and $Z^b$ is amino.

19. A compound of claim 15 wherein $Z^a$ is ethoxy and $Z^b$ is methoxy.

20. A compound of claim 15 wherein $Z^a$ is n-propoxy and $Z^b$ is methoxy.

21. A compound of the formula

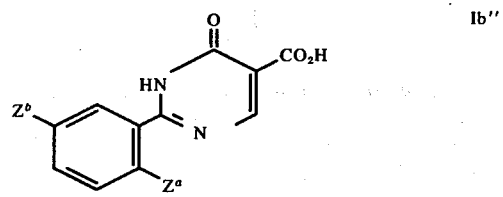

Ib'' wherein $Z^a$ is methoxy, ethoxy, n-propoxy, isopropoxy, n-butoxy, isobutoxy, sec-butoxy, allyloxy or cyclopropylmethoxy and $Z^b$ is methoxy, ethoxy, n-propoxy, isopropoxy, n-butoxy, isobutoxy, sec-butoxy, allyloxy, cyclopropylmethoxy, chlorine, amino, dimethylamino or carbethoxy, or a pharmaceutically acceptable salt thereof.

22. A compound of claim 21 wherein $Z^a$ is methoxy and $Z^b$ is methoxy, or a pharmaceutically acceptable salt thereof.

23. A compound of claim 21 wherein $Z^a$ is ethoxy and $Z^b$ is chlorine, or a pharmaceutically acceptable salt thereof.

24. A compound of claim 21 wherein $Z^a$ is ethoxy and $Z^b$ is amino, or a pharmaceutically acceptable salt thereof.

25. A compound of claim 21 wherein $Z^a$ is ethoxy and $Z^b$ is methoxy, or a pharmaceutically acceptable salt thereof.

26. A compound of claim 21 wherein $Z^a$ is ethoxy and $Z^b$ is dimethylamino, or a pharmaceutically acceptable salt thereof.

27. A compound of claim 21 wherein $Z^a$ is n-propoxy and $Z^b$ is methoxy, or a pharmaceutically acceptable salt thereof.

28. A compound is the formula

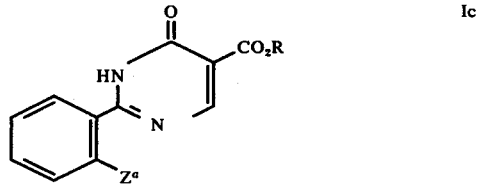

Ic wherein $Z^a$ is —O—$C_2$—$C_6$ alkyl, —O—$C_2$—$C_6$ alkenyl, or

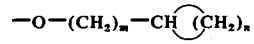

in which m is 0 or an integer from 1 to 6 and n is an integer from 2 to 7, and R is selected from the group consisting of hydrogen, $C_1$–$C_{10}$ alkyl, pivaloyloxymethyl, acetoxymethyl and methoxymethyl, or a pharmaceutically acceptable salt thereof.

29. A compound of claim 28 wherein $Z^a$ is $-O-C_2-C_6$ alkyl, $-O-C_2-C_6$ alkenyl or $$-O-(CH_2)_m-CH(CH_2)_n$$

in which $m$ is 0 or an integer from 1 to 4 and $n$ is an integer from 2 to 5, or a pharmaceutically acceptable salt thereof.

30. A compound of claim 28 wherein $Z^a$ is ethoxy, n-propoxy, isopropoxy, n-butoxy, isobutoxy, sec-butoxy, allyloxy or cyclopropylmethoxy, or a pharmaceutically acceptable salt thereof.

31. A compound of claim 28 wherein R is $C_1-C_6$ alkyl.

32. A compound of claim 28 wherein R is pivaloyloxymethyl, acetoxymethyl or methoxymethyl.

33. A compound of claim 28 wherein R is hydrogen.

34. A compound of the formula

Ic′

[Structure: benzene ring with $Z^a$ substituent, connected via C=N to HN-C(=O)-CH=CH-N with CO$_2$C$_2$H$_5$ group]

wherein $Z^a$ is ethoxy, n-propoxy, isopropoxy, n-butoxy, isobutoxy, sec-butoxy, allyloxy or cyclopropylmethoxy.

35. A compound of claim 34 wherein $Z^a$ is ethoxy.
36. A compound of claim 34 wherein $Z^a$ is n-propoxy.
37. A compound of claim 34 wherein $Z^a$ is isopropoxy.
38. A compound of claim 34 wherein $Z^a$ is n-butoxy.
39. A compound of claim 34 wherein $Z^a$ is sec-butoxy.
40. The (+) optical isomer of the compound of claim 39.
41. The (−) optical isomer of the compound of claim 39.
42. A compound of claim 34 wherein $Z^a$ is isobutoxy.
43. A compound of claim 34 wherein $Z^a$ is allyloxy.
44. A compound of claim 34 wherein $Z^a$ is cyclopropylmethoxy.
45. A compound of the formula Ic″

[Structure: benzene ring with $Z^a$ substituent, connected via C=N to HN-C(=O)-CH=CH-N with CO$_2$H group]

wherein $Z^a$ is ethoxy, n-propoxy, isopropoxy, n-butoxy, isobutoxy, sec-butoxy, allyloxy or cyclopropylmethoxy, or a pharmaceutically acceptable salt thereof.

46. The sodium or potassium salt of a compound of claim 45.
47. A compound of claim 45 wherein $Z^a$ is ethoxy, or a pharmaceutically acceptable salt thereof.
48. The sodium salt of the compound of claim 47.
49. The potassium salt of the compound of claim 47.
50. A compound of claim 45 wherein $Z^a$ is n-propoxy, or a pharmaceutically acceptable salt thereof.
51. The sodium salt of the compound of claim 50.
52. The potassium salt of the compound of claim 50.
53. A compound of claim 45 wherein $Z^a$ is isopropoxy, or a pharmaceutically acceptable salt thereof.
54. The sodium salt of the compound of claim 53.
55. The potassium salt of the compound of claim 53.
56. A compound of claim 45 wherein $Z^a$ is n-butoxy, or a pharmaceutically acceptable salt thereof.
57. A compound of claim 45 wherein $Z^a$ is isobutoxy, or a pharmaceutically acceptable salt thereof.
58. A compound of claim 45 wherein $Z^a$ is sec-butoxy, or a pharmaceutically acceptable salt thereof.
59. The (+) optical isomer of the compound of claim 58, or a pharmaceutically acceptable salt thereof.
60. The (−) optical isomer of the compound of claim 58, or a pharmaceutically acceptable salt thereof.
61. A compound of claim 45 wherein $Z^a$ is allyloxy, or a pharmaceutically acceptable salt thereof.
62. A compound of claim 45 wherein $Z^a$ is cyclopropylmethoxy, or a pharmaceutically acceptable salt thereof.

* * * * *

UNITED STATES PATENT AND TRADEMARK OFFICE
CERTIFICATE OF CORRECTION

PATENT NO. : 4,031,093
DATED : June 21, 1977
INVENTOR(S) : Peter Frederick Juby and Richard Anthony Partyka It is certified that error appears in the above-identified patent and that said Letters Patent are hereby corrected as shown below:

In column 3, line 16, "$R^b$" should read --$R^c$--.

In column 3, line 21, insert --in which $R^b$ is $C_1-C_6$ alkyl,-- after "$-O-\overset{\overset{O}{\|}}{C}-NHR^b$".

In column 3, line 22, insert -- $-O(CH_2)_k OH$-- before "in which".

In column 5, line 15, delete "$-O-(CH_2)_m-$".

In column 5, line 67, delete "$-O-(CH_2)_m-$".

In columns 9-10, formula I', delete double bond between positions 1 and 2 and insert double bond between positions 2 and 3.

In column 17, Table I, Example 7, "$OCH(_3)_2$" should read --$OCH(CH_3)_2$--.

In Claim 2, line 49, insert --or carb($C_1-C_6$)alkoxy,-- after "di($C_1-C_6$)alkylamino".

UNITED STATES PATENT OFFICE
CERTIFICATE OF CORRECTION

Patent No. 4,031,093          Dated  June 21, 1977

Inventor(s)  Peter Frederick Juby, et al

It is certified that error appears in the above-identified patent and that said Letters Patent are hereby corrected as shown below:

In Claim 13, line 48, insert --or carb($C_1$-$C_6$)-- before "alkoxy"

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*